(12) United States Patent
Gan et al.

(10) Patent No.: US 10,004,753 B2
(45) Date of Patent: Jun. 26, 2018

(54) METHODS FOR TREATING TAUOPATHY

(71) Applicant: The J. David Gladstone Institutes, San Francisco, CA (US)

(72) Inventors: Li Gan, Burlingame, CA (US); Xu Chen, San Francisco, CA (US); Min Xie, Daly City, CA (US); Eric M. Verdin, Mill Valley, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 0 days. days.

(21) Appl. No.: 15/543,199

(22) PCT Filed: Jan. 15, 2016

(86) PCT No.: PCT/US2016/013700
§ 371 (c)(1),
(2) Date: Jul. 12, 2017

(87) PCT Pub. No.: WO2016/115520
PCT Pub. Date: Jul. 21, 2016

(65) Prior Publication Data
US 2017/0368080 A1 Dec. 28, 2017

Related U.S. Application Data

(60) Provisional application No. 62/104,645, filed on Jan. 16, 2015.

(51) Int. Cl.
| | | |
|---|---|---|
| *A61K 31/618* | (2006.01) |
| *A61K 47/54* | (2017.01) |
| *A61K 47/55* | (2017.01) |
| *A61K 47/64* | (2017.01) |
| *A61K 47/69* | (2017.01) |
| *A61K 9/00* | (2006.01) |
| *A61K 9/127* | (2006.01) |
| *A61K 9/50* | (2006.01) |

(52) U.S. Cl.
CPC .......... *A61K 31/618* (2013.01); *A61K 9/0053* (2013.01); *A61K 9/127* (2013.01); *A61K 9/5031* (2013.01); *A61K 47/548* (2017.08); *A61K 47/549* (2017.08); *A61K 47/55* (2017.08); *A61K 47/64* (2017.08); *A61K 47/6933* (2017.08)

(58) Field of Classification Search
None
See application file for complete search history.

(56) References Cited

U.S. PATENT DOCUMENTS

| | | | |
|---|---|---|---|
| 5,404,871 A | 4/1995 | Goodman et al. |
| 5,497,763 A | 3/1996 | Lloyd et al. |
| 5,542,410 A | 8/1996 | Goodman et al. |
| 5,544,646 A | 8/1996 | Lloyd et al. |
| 5,631,015 A | 5/1997 | Bezwada et al. |
| 5,660,166 A | 8/1997 | Lloyd et al. |
| 5,718,222 A | 2/1998 | Lloyd et al. |
| 5,736,371 A | 4/1998 | Samain et al. |
| 5,740,794 A | 4/1998 | Smith et al. |
| 5,775,320 A | 7/1998 | Patton et al. |
| 6,187,330 B1 | 2/2001 | Wang et al. |
| 6,296,842 B1 | 10/2001 | Jaworowicz et al. |
| 6,303,148 B1 | 10/2001 | Hennink et al. |
| 6,346,269 B1 | 2/2002 | Hsiao et al. |
| 6,379,701 B1 | 4/2002 | Tracy et al. |
| 6,458,398 B1 | 10/2002 | Smith et al. |
| 6,630,155 B1 | 10/2003 | Chandrashekar et al. |
| 6,699,504 B2 | 3/2004 | Rowe et al. |
| 6,703,037 B1 | 3/2004 | Hubbell et al. |
| 7,750,047 B2 | 7/2010 | Kundu et al. |
| 9,040,521 B2 | 5/2015 | Gan |
| 9,585,907 B2 | 3/2017 | Gan |
| 2012/0225864 A1 | 9/2012 | Gan |
| 2013/0184353 A1 | 7/2013 | Dickey et al. |
| 2014/0011776 A1 | 1/2014 | Vassiliou et al. |
| 2017/0121268 A1 | 5/2017 | Romeiro et al. |

FOREIGN PATENT DOCUMENTS

| | | |
|---|---|---|
| WO | WO 2011056300 | 5/2001 |
| WO | WO 2013090405 | 6/2013 |
| WO | WO 2014177593 | 11/2014 |
| WO | WO 2015176153 | 11/2015 |

OTHER PUBLICATIONS

Bas A. In 'T Veld, Annemieke Ruitenberg, Albert Hofman, Lenore J. Launer, Cornelia M. van Duijn, Theo Stijnen, Monique M. B. Breteler, Bruno H. C. Stricker, Nonsteroidal Antiinflammatory Drugs and the Risk of Alzheimer's Disease, Nov. 22, 2001, New England Journal of Medicine, vol. 345, No. 21, 1515-1521.*

Burns et al. (2009) "Fluorescent silica nanoparticles with efficient urinary excretion for nanomedicine"; Nano Letters. 9(1): pp. 442-448.

Faizi, M., et al. (2012) "Thy1-hAPP(Lond/Swe+) mouse model of Alzheimer's disease displays broad behavioral deficits in sensorimotor, cognitive and social function"; Brain Behav 2(2); pp. 142-154.

Hasegawa, et al. (1985) "Application of solid dispersions of Nifedipine with enteric coating agent to prepare a sustained-release dosage form"; Chem. Pharm. Bull. 33(4); pp. 1615-1619.

Hasegawa, et al (1988) "Super Saturation Mechanism of Drugs from Solid Dispersions with Enteric Coating Agents"; Chem. Pharm. Bull. 36(12); pp. 4941-4950.

Jain et al. (2005) "Iron oxide nanoparticles for sustained delivery of anticancer agents"; Mol. Pharm. 2(3); pp. 194-205.

Koida, et al. (1987) "Studies on Dissolution Mechanism of Drugs from Ethyl Cellulose Microcapsules"; Chem. Pharm. Bull. 35(4): pp. 1538-1545.

(Continued)

*Primary Examiner* — Adam M Weidner

(74) *Attorney, Agent, or Firm* — Michael B. Rubin; Bozicevic, Field & Francis LLP

(57) ABSTRACT

The present disclosure provides methods of reducing the level of acetylated Tau in a neuron or a glial cell in an individual, the methods involving administering to the individual a prodrug that is converted in the individual to salicylate. The present disclosure provides methods of treating a tauopathy in an individual, the methods involving administering to the individual a prodrug that is converted in the individual to salicylate.

20 Claims, 13 Drawing Sheets

(56) References Cited

OTHER PUBLICATIONS

Klessig, Daniel F., et al (2016) "Multiple Targets of Salicylic Acid and its Derivatives in Plants and Animals"; *Front Immunol.* 7(206); pp. 1-10.
Langer (1990) "New methods of drug delivery"; *Science* 249; pp. 1527-1533.
Min, Sang-Won, et al (2010) "Acetylation of Tau Inhibits Its Degradation and Contributes to Tauopathy"; *Neuron.* 67(6); pp. 953-966.
Min, Sang-Won, et al (2015) "Critical Role of Acetylation in Tau-Mediated Neurodegeneration and Cognitive Deficits"; *Nat Med.* 21(10); pp. 1154-1162.
Porter S.C. et al. (1970) "The Properties of Enteric Tablet Coatings Made From Polyvinyl Acetate-phthalate and Cellulose acetate Phthalate"; *J. Pharm. Pharmacol.* 22:42p.
Raghunathan, Y. et al. (1981) "Sustained-released drug delivery system I: Coded ion-exchange resin systems for phenylpropanolamine and other drugs" *J. Pharm. Sciences* 70; pp. 379-384.
Takada, Shigeyuki, (1997) "Utilization of an Amorphous Form of a Water-Soluble GPIIb/IIIa Antagonist for Controlled Release From Biodegradable Micro spheres"; *Pharm. Res.* 14:1146-1150.
Weidner, et al (2016) "Amorfrutin C Induces Apoptosis and Inhibits Proliferation in Colon Cancer Cells through Targeting Mitochondria"; *J Nat Prod.* 79(1); pp. 2-12.

\* cited by examiner

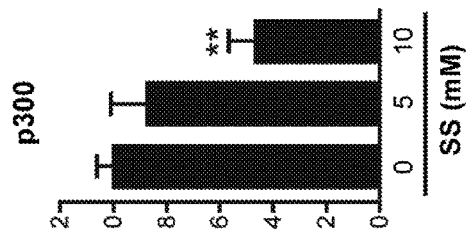
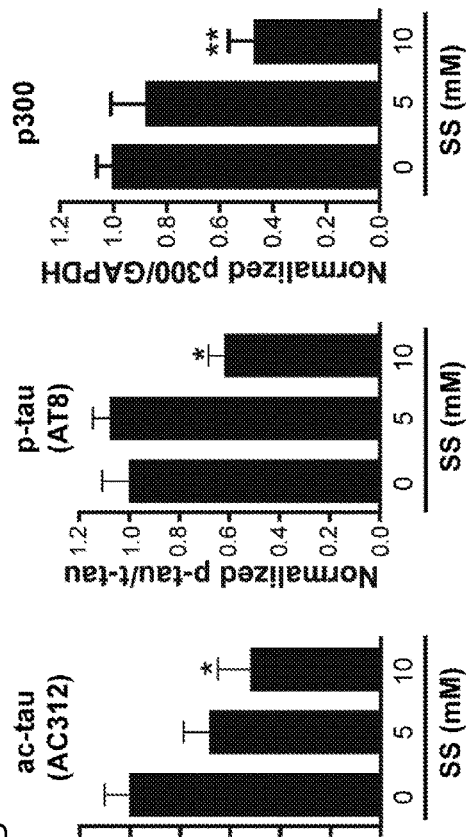
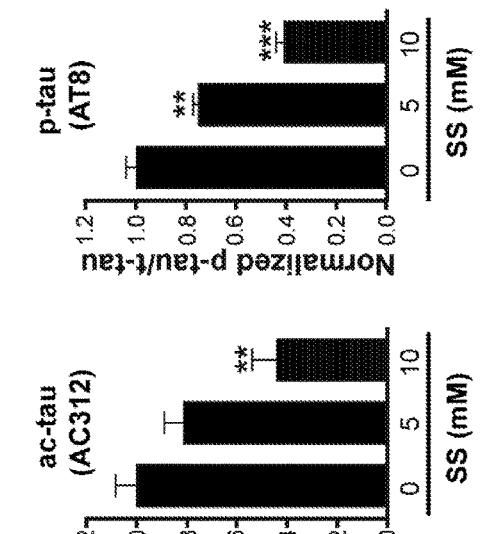
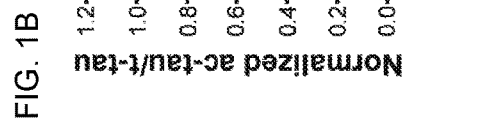
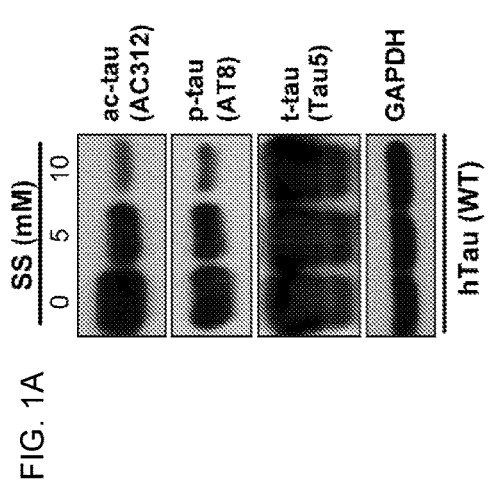
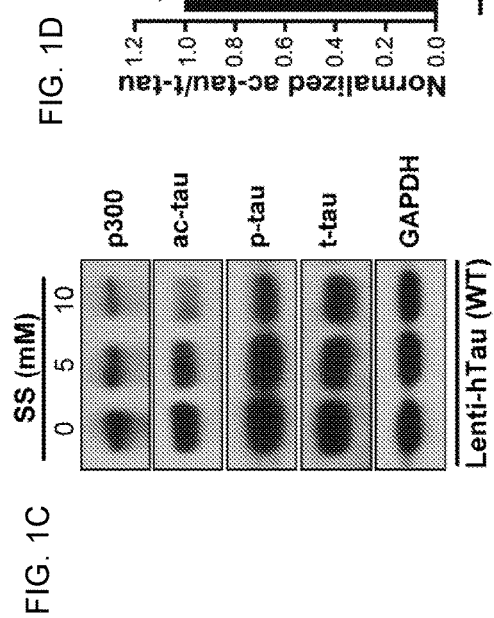
FIG. 1A  FIG. 1B  FIG. 1C  FIG. 1D

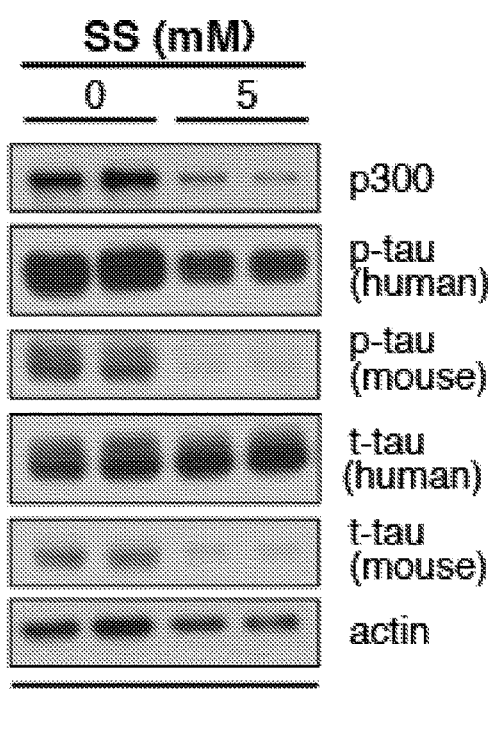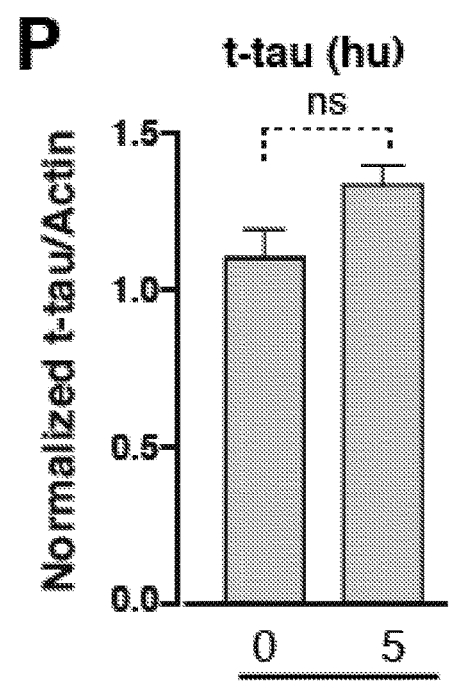
FIG. 2A
FIG. 2B

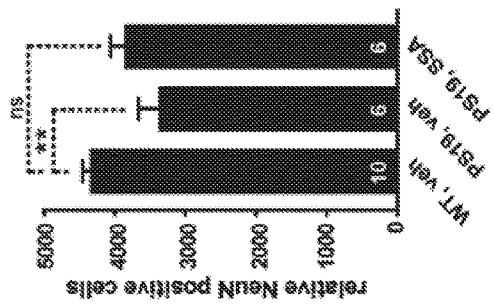
FIG. 4B
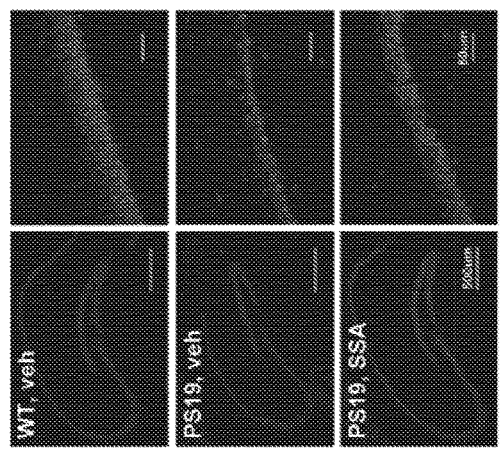
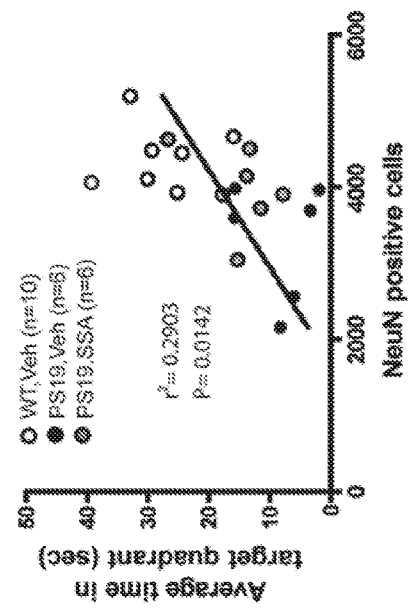
FIG. 4C
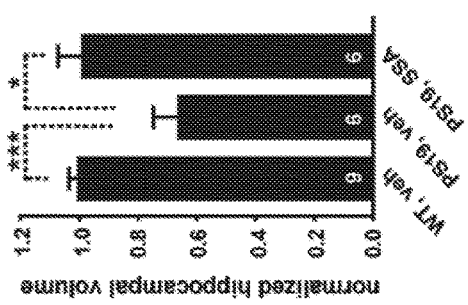
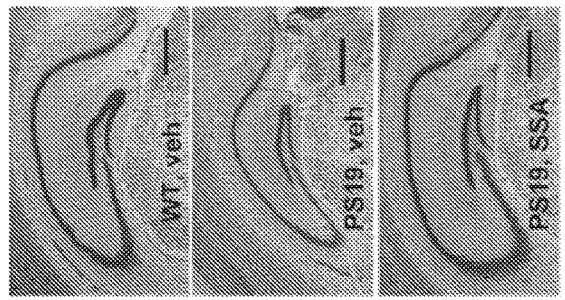
FIG. 4A

FIG. 6A

```
seq_id_1    MAEPRQEFEVMEDHAGTYGLGDRKDQGGYTMHQDQEGDTDAGLKESPLQTPTEDGSEEPG    60
seq_id_2    MAEPRQEFEVMEDHAGTYGLGDRKDQGGYTMHQDQEGDTDAGLK---------------    44
seq_id_3    MAEPRQEFEVMEDHAGTYGLGDRKDQGGYTMHQDQEGDTDAGLK---------------    44
seq_id_4    MAEPRQEFEVMEDHAGTYGLGDRKDQGGYTMHQDQEGDTDAGLKESPLQTPTEDGSEEPG    60
seq_id_6    MAEPRQEFEVMEDHAGTYGLGDRKDQGGYTMHQDQEGDTDAGLKESPLQTPTEDGSEEPG    60
seq_id_5    MAEPRQEFEVMEDHAGTYGLGDRKDQGGYTMHQDQEGDTDAGLKESPLQTPTEDGSEEPG    60
            ******************************************* seq_id_1    SETSDAKSTPTAEDVTAPLVDEGAPGKQAAAQPHTEIPEGTTAEEAGIGDTPSLEDEAAG   120
seq_id_2    ------------------------------------AEEAGIGDTPSLEDEAAG        62
seq_id_3    ------------------------------------AEEAGIGDTPSLEDEAAG        62
seq_id_4    SETSDAKSTP-----------------------------TAEAEEAGIGDTPSLEDEAAG  91
seq_id_6    SETSDAKSTPTAEDVTAPLVDEGAPGKQAAAQPHTEIPEGTTAEEAGIGDTPSLEDEAAG   120
seq_id_5    SETSDAKSTPTAEDVTAPLVDEGAPGKQAAAQPHTEIPEGTTAEEAGIGDTPSLEDEAAG   120
                                                ****************** seq_id_1    HVTQ--------------------------------------------------------  124
seq_id_2    HVTQ--------------------------------------------------------   66
seq_id_3    HVTQ--------------------------------------------------------   66
seq_id_4    HVTQ--------------------------------------------------------   95
seq_id_6    HVTQEPESGKVVQEGFLREPGPPGLSHQLMSGMPGAPLLPEGPREATRQPSGTGPEDTEG   180
seq_id_5    HVTQEPESGKVVQEGFLREPGPPGLSHQLMSGMPGAPLLPEGPREATRQPSGTGPEDTEG   180
            **** seq_id_1    ------------------------------------------------------------
seq_id_2    ------------------------------------------------------------
seq_id_3    ------------------------------------------------------------
seq_id_4    ------------------------------------------------------------
seq_id_6    GRHAPELLKHQLLGDLHQEGPPLKGAGGKERPGSKEEVDEDRDVDESSPQDSPPSKASPA   240
seq_id_5    GRHAPELLKHQLLGDLHQEGPPLKGAGGKERPGSKEEVDEDRDVDESSPQDSPPSKASPA   240
```

FIG. 6B

```
seq_id_1  ------------------------------------------------------------        -
seq_id_2  ------------------------------------------------------------        -
seq_id_3  ------------------------------------------------------------        -
seq_id_4  ------------------------------------------------------------        -
seq_id_6  QDGRPPQTAAREATSIPGFPAEGAIPLPVDFLSKVSTEIPASEPDGPSVGRAKGQDAPLE      300
seq_id_5  QDGRPPQTAAREATSIPGFPAEGAIPLPVDFLSKVSTEIPASEPDGPSVGRAKGQDAPLE      300 seq_id_1  ------------------------------------------------------------        -
seq_id_2  ------------------------------------------------------------        -
seq_id_3  ------------------------------------------------------------        -
seq_id_4  ------------------------------------------------------------        -
seq_id_6  FTFHVEITPNVQKEQAHSEEHLGRAAFPGAPGEGPEARGPSLGEDTKEADLPEPSEKQPA      360
seq_id_5  FTFHVEITPNVQKEQAHSEEHLGRAAFPGAPGEGPEARGPSLGEDTKEADLPEPSEKQPA      360 seq_id_1  ----------------ARMVSKSKDGTGSDDKKAK-------------------------      143
seq_id_2  ----------------ARMVSKSKDGTGSDDKKAK-------------------------       85
seq_id_3  ----------------ARMVSKSKDGTGSDDKKAK-------------------------       85
seq_id_4  ----------------ARMVSKSKDGTGSDDKKAK-------------------------      114
seq_id_6  AAPRGKPVSRVPQLKARMVSKSKDGTGSDDKKAKTSTRSSAKTLKNRPCLSPKHPTPGSS      420
seq_id_5  AAPRGKPVSRVPQLKARMVSKSKDGTGSDDKKAKTSTRSSAKTLKNRPCLSPKHPTPGSS      420
                          ****************** seq_id_1  ----------------------------GADGKTKIATPRGAAPPGQK                  163
seq_id_2  ----------------------------GADGKTKIATPRGAAPPGQK                  105
seq_id_3  ----------------------------GADGKTKIATPRGAAPPGQK                  105
seq_id_4  ----------------------------GADGKTKIATPRGAAPPGQK                  134
seq_id_6  DPLIQPSSPAVCPEPPSSPKHVSSVTSRTGSSGAKEMLKGADGKTKIATPRGAAPPGQK       480
seq_id_5  DPLIQPSSPAVCPEPPSSPKHVSSVTSRTGSSGAKEMLKGADGKTKIATPRGAAPPGQK       480
                                      ************************
```

FIG. 6C

```
seq_id_1  GQANATRIPAKTPPAPKTPPSS--------------------GEPPKSGDRSGYSSPGSPGT  205
seq_id_2  GQANATRIPAKTPPAPKTPPSS--------------------GEPPKSGDRSGYSSPGSPGT  147
seq_id_3  GQANATRIPAKTPPAPKTPPSS--------------------GEPPKSGDRSGYSSPGSPGT  147
seq_id_4  GQANATRIPAKTPPAPKTPPSS--------------------GEPPKSGDRSGYSSPGSPGT  176
seq_id_6  GQANATRIPAKTPPAPKTPPSSATKQVQRRPPPAGPRSERGEPPKSGDRSGYSSPGSPGT   540
seq_id_5  GQANATRIPAKTPPAPKTPPSS--------------------GEPPKSGDRSGYSSPGSPGT  522
          ********************                    **************** seq_id_1  PGSRSRTPSLPTPPTREPKKVAVVRTPPKSPSSAKSRLQTAPVPMPDLKNVKSKIGSTEN  265
seq_id_2  PGSRSRTPSLPTPPTREPKKVAVVRTPPKSPSSAKSRLQTAPVPMPDLKNVKSKIGSTEN  207
seq_id_3  PGSRSRTPSLPTPPTREPKKVAVVRTPPKSPSSAKSRLQTAPVPMPDLKNVKSKIGSTEN  207
seq_id_4  PGSRSRTPSLPTPPTREPKKVAVVRTPPKSPSSAKSRLQTAPVPMPDLKNVKSKIGSTEN  236
seq_id_6  PGSRSRTPSLPTPPTREPKKVAVVRTPPKSPSSAKSRLQTAPVPMPDLKNVKSKIGSTEN  600
seq_id_5  PGSRSRTPSLPTPPTREPKKVAVVRTPPKSPSSAKSRLQTAPVPMPDLKNVKSKIGSTEN  582
          ************************************************************ seq_id_1  LKHQPGGGKVQIINKKLDLSNVQSKCGSKDNIKHVPGGGSVQIVYKPVDLSKVTSKCGSL  325
seq_id_2  LKHQPGGGKVQIINKKLDLSNVQSKCGSKDNIKHVPGGGSVQIVYKPVDLSKVTSKCGSL  267
seq_id_3  LKHQPGGGK---------------------------------VQIVYKPVDLSKVTSKCGSL  236
seq_id_4  LKHQPGGGKVQIINKKLDLSNVQSKCGSKDNIKHVPGGGSVQIVYKPVDLSKVTSKCGSL  296
seq_id_6  LKHQPGGGKVQIINKKLDLSNVQSKCGSKDNIKHVPGGGSVQIVYKPVDLSKVTSKCGSL  660
seq_id_5  LKHQPGGGKVQIINKKLDLSNVQSKCGSKDNIKHVPGGGSVQIVYKPVDLSKVTSKCGSL  642
          *******                                 **************** seq_id_1  GNIHHKPGGGQVEVKSEKLDFKDRVQSKIGSLDNITHVPGGGNKKIETHKLTFRENAKAK  385
seq_id_2  GNIHHKPGGGQVEVKSEKLDFKDRVQSKIGSLDNITHVPGGGNKKIETHKLTFRENAKAK  327
seq_id_3  GNIHHKPGGGQVEVKSEKLDFKDRVQSKIGSLDNITHVPGGGNKKIETHKLTFRENAKAK  296
seq_id_4  GNIHHKPGGGQVEVKSEKLDFKDRVQSKIGSLDNITHVPGGGNKKIETHKLTFRENAKAK  356
seq_id_6  GNIHHKPGGGQVEVKSEKLDFKDRVQSKIGSLDNITHVPGGGNKKIETHKLTFRENAKAK  720
seq_id_5  GNIHHKPGGGQVEVKSEKLDFKDRVQSKIGSLDNITHVPGGGNKKIETHKLTFRENAKAK  702
          ************************************************************
```

FIG. 6D

```
seq_id_1  TDHGAEIVYKSPVVSGDTSPRHLSNVSSTGSIDMVDSPQLATLADEVSASLAKQGL  441
seq_id_2  TDHGAEIVYKSPVVSGDTSPRHLSNVSSTGSIDMVDSPQLATLADEVSASLAKQGL  383
seq_id_3  TDHGAEIVYKSPVVSGDTSPRHLSNVSSTGSIDMVDSPQLATLADEVSASLAKQGL  352
seq_id_4  TDHGAEIVYKSPVVSGDTSPRHLSNVSSTGSIDMVDSPQLATLADEVSASLAKQGL  412
seq_id_6  TDHGAEIVYKSPVVSGDTSPRHLSNVSSTGSIDMVDSPQLATLADEVSASLAKQGL  776
seq_id_5  TDHGAEIVYKSPVVSGDTSPRHLSNVSSTGSIDMVDSPQLATLADEVSASLAKQGL  758
          *******************************************************
```

FIG. 7

```
mouse  MADPRQEFDTMEDHAG---------DYTLLQDQEGDMDHGLKESPPQPPADDGAEEPG        49
rat    MAEPRQEFDTMEDQAG---------DYTMLQDQEGDMDHGLKESPPQPPADDGSEEPG        49
human  MAEPRQEFEVMEDHAGTYGLGDRKDQGGYTMHQDQEGDTDAGLKESPLQTPTEDGSEEPG       60
       **:******:****:**         .**: ***:********** :.*:*.**:****

mouse  SETSDAKSTPTAEDVTAPLVDERAPDKQAAAQPHTEIPEGITAEEAGIGDTPNQEDQAAG     109
rat    SETSDAKSTPTAEDVTAPLVEERAPDKQATAQSHTEIPEGTTAEEAGIGDTPNMEDQAAG     109
human  SETSDAKSTPTAEDVTAPLVDEGAPGKQAAAQPHTEIPEGTTAEEAGIGDTPSLEDEAAG     120
       ********************:*  *:.***:******. :*** mouse  HVTQARVA--SKDRTGNDEKKAKGADGKTGAKIATPRGAASPAQKGTSNATRIPAKTTPS     167
rat    HVTQARVAGVSKDRTGNDEKKAKGADGKTGAKIATPRGAATPGQKGTSNATRIPAKTTPS     169
human  HVTQARMVSKSKDGTGSDDKKAKGADGKT--KIATPRGAAPPGQKGQANATRIPAKTPPA     178
       ******:.  *** **.*:*********  ********: *.***:.:*********.:

mouse  PKTPPGSGEPPKSGERSGYSSPGSPGSPGTPGSRSRTPSLPTPPTREPKKVAVVRTPPKSPSA     227
rat    PKTPPGSGEPPKSGERSGYSSPGSPGSPGTPGSRSRTPSLPTPPTREPKKVAVVRTPPKSPSA     229
human  PKTPPSSGEPPKSGDRSGYSSPGSPGSPGTPGSRSRTPSLPTPPTREPKKVAVVRTPPKSPSS     238
       *****.********:***:*.:*******************************.*****.

mouse  SKSRLQTAPVPMPDLKNVRSKIGSTENLKHQPGGGKVQIINKKLDLSNVQSKCGSKDNIK     287
rat    SKSRLQTAPVPMPDLKNVRSKIGSTENLKHQPGGGKVQIINKKLDLSNVQSKCGSKDNIK     289
human  AKSRLQTAPVPMPDLKNVKSKIGSTENLKHQPGGGKVQIINKKLDLSNVQSKCGSKDNIK     298
       :***************:*************************************** mouse  HVPGGGSVQIVYKPVDLSKVTSKCGSLGNIHHKPGGGQVEVKSEKLDFKDRVQSKIGSLD     347
rat    HVPGGGSVQIVYKPVDLSKVTSKCGSLGNIHHKPGGGQVEVKSEKLDFKDRVQSKIGSLD     349
human  HVPGGGSVQIVYKPVDLSKVTSKCGSLGNIHHKPGGGQVEVKSEKLDFKDRVQSKIGSLD     358
       ************************************************************ mouse  NITHVPGGGNKKIETHKLTFRENAKAKTDHGAEIVYKSPVVSGDTSPRHLSNVSSTGSID     407
rat    NITHVPGGGNKKIETHKLTFRENAKAKTDHGAEIVYKSPVVSGDTSPRHLSNVSSTGSID     409
human  NITHVPGGGNKKIETHKLTFRENAKAKTDHGAEIVYKSPVVSGDTSPRHLSNVSSTGSID     418
       ************************************************************ mouse  MVDSPQLATLADEVSASLAKQGL  430   (SEQ ID NO:8)
rat    MVDSPQLATLADEVSASLAKQGL  432   (SEQ ID NO:7)
human  MVDSPQLATLADEVSASLAKQGL  441   (SEQ ID NO:1)
       ***********************
```

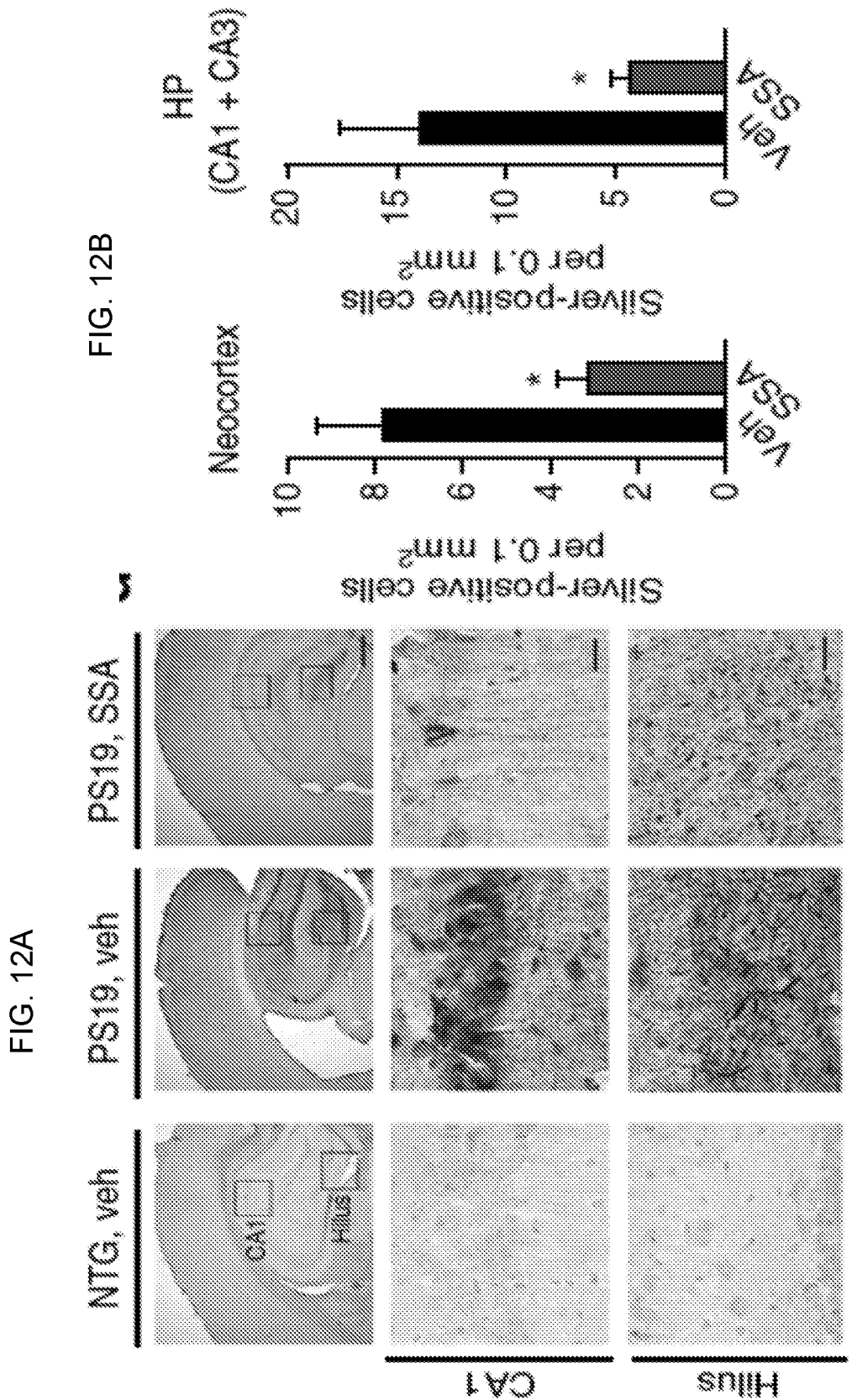

SEQUENCE LISTING

```
<160> NUMBER OF SEQ ID NOS: 8

<210> SEQ ID NO 1
<211> LENGTH: 441
<212> TYPE: PRT
<213> ORGANISM: Homo sapiens

<400> SEQUENCE: 1
```

| | | | | | | | | | | | | | | | |
|---|---|---|---|---|---|---|---|---|---|---|---|---|---|---|---|
| Met | Ala | Glu | Pro | Arg | Gln | Glu | Phe | Glu | Val | Met | Glu | Asp | His | Ala | Gly |
| 1 | | | | 5 | | | | | 10 | | | | | 15 | |
| Thr | Tyr | Gly | Leu | Gly | Asp | Arg | Lys | Asp | Gln | Gly | Gly | Tyr | Thr | Met | His |
| | | | 20 | | | | | 25 | | | | | 30 | | |
| Gln | Asp | Gln | Glu | Gly | Asp | Thr | Asp | Ala | Gly | Leu | Lys | Glu | Ser | Pro | Leu |
| | | 35 | | | | | 40 | | | | | 45 | | | |
| Gln | Thr | Pro | Thr | Glu | Asp | Gly | Ser | Glu | Glu | Pro | Gly | Ser | Glu | Thr | Ser |
| | 50 | | | | | 55 | | | | | 60 | | | | |
| Asp | Ala | Lys | Ser | Thr | Pro | Thr | Ala | Glu | Asp | Val | Thr | Ala | Pro | Leu | Val |
| 65 | | | | | 70 | | | | | 75 | | | | | 80 |
| Asp | Glu | Gly | Ala | Pro | Gly | Lys | Gln | Ala | Ala | Ala | Gln | Pro | His | Thr | Glu |
| | | | | 85 | | | | | 90 | | | | | 95 | |
| Ile | Pro | Glu | Gly | Thr | Thr | Ala | Glu | Glu | Ala | Gly | Ile | Gly | Asp | Thr | Pro |
| | | | 100 | | | | | 105 | | | | | 110 | | |
| Ser | Leu | Glu | Asp | Glu | Ala | Ala | Gly | His | Val | Thr | Gln | Ala | Arg | Met | Val |
| | | 115 | | | | | 120 | | | | | 125 | | | |
| Ser | Lys | Ser | Lys | Asp | Gly | Thr | Gly | Ser | Asp | Asp | Lys | Lys | Ala | Lys | Gly |
| | 130 | | | | | 135 | | | | | 140 | | | | |
| Ala | Asp | Gly | Lys | Thr | Lys | Ile | Ala | Thr | Pro | Arg | Gly | Ala | Ala | Pro | Pro |
| 145 | | | | | 150 | | | | | 155 | | | | | 160 |
| Gly | Gln | Lys | Gly | Gln | Ala | Asn | Ala | Thr | Arg | Ile | Pro | Ala | Lys | Thr | Pro |
| | | | | 165 | | | | | 170 | | | | | 175 | |
| Pro | Ala | Pro | Lys | Thr | Pro | Pro | Ser | Ser | Gly | Glu | Pro | Pro | Lys | Ser | Gly |
| | | | 180 | | | | | 185 | | | | | 190 | | |
| Asp | Arg | Ser | Gly | Tyr | Ser | Ser | Pro | Gly | Ser | Pro | Gly | Thr | Pro | Gly | Ser |
| | | 195 | | | | | 200 | | | | | 205 | | | |
| Arg | Ser | Arg | Thr | Pro | Ser | Leu | Pro | Thr | Pro | Pro | Thr | Arg | Glu | Pro | Lys |
| | 210 | | | | | 215 | | | | | 220 | | | | |
| Lys | Val | Ala | Val | Val | Arg | Thr | Pro | Pro | Lys | Ser | Pro | Ser | Ser | Ala | Lys |
| 225 | | | | | 230 | | | | | 235 | | | | | 240 |
| Ser | Arg | Leu | Gln | Thr | Ala | Pro | Val | Pro | Met | Pro | Asp | Leu | Lys | Asn | Val |
| | | | | 245 | | | | | 250 | | | | | 255 | |

```
Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
            290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                    325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
            370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                    405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 2
<211> LENGTH: 383
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
        130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190
```

```
Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
        210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
            245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
        290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
            325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
            355                 360                 365

Thr Leu Ala Asp Glu Val Ser Ala Ser Leu Ala Lys Gln Gly Leu
        370                 375                 380

<210> SEQ ID NO 3
<211> LENGTH: 352
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
```

```
                180              185              190
Pro Asp Leu Lys Asn Val Lys Ser Lys Ile Gly Ser Thr Glu Asn Leu
            195                  200              205
Lys His Gln Pro Gly Gly Gly Lys Val Gln Ile Val Tyr Lys Pro Val
            210                  215                  220
Asp Leu Ser Lys Val Thr Ser Lys Cys Gly Ser Leu Gly Asn Ile His
225                  230                  235                  240
His Lys Pro Gly Gly Gly Gln Val Glu Val Lys Ser Glu Lys Leu Asp
                245                  250                  255
Phe Lys Asp Arg Val Gln Ser Lys Ile Gly Ser Leu Asp Asn Ile Thr
            260                  265                  270
His Val Pro Gly Gly Gly Asn Lys Lys Ile Glu Thr His Lys Leu Thr
            275                  280                  285
Phe Arg Glu Asn Ala Lys Ala Lys Thr Asp His Gly Ala Glu Ile Val
            290                  295                  300
Tyr Lys Ser Pro Val Val Ser Gly Asp Thr Ser Pro Arg His Leu Ser
305                  310                  315                  320
Asn Val Ser Ser Thr Gly Ser Ile Asp Met Val Asp Ser Pro Gln Leu
                325                  330                  335
Ala Thr Leu Ala Asp Glu Val Ser Ala Ser Leu Ala Lys Gln Gly Leu
            340                  345                  350

<210> SEQ ID NO 4
<211> LENGTH: 412
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Ala Glu Glu Ala Gly Ile Gly
65                  70                  75                  80
Asp Thr Pro Ser Leu Glu Asp Glu Ala Ala Gly His Val Thr Gln Ala
                85                  90                  95
Arg Met Val Ser Lys Ser Lys Asp Gly Thr Gly Ser Asp Asp Lys Lys
            100                 105                 110
Ala Lys Gly Ala Asp Gly Lys Thr Lys Ile Ala Thr Pro Arg Gly Ala
        115                 120                 125
Ala Pro Pro Gly Gln Lys Gly Gln Ala Asn Ala Thr Arg Ile Pro Ala
    130                 135                 140
Lys Thr Pro Pro Ala Pro Lys Thr Pro Pro Ser Ser Gly Glu Pro Pro
145                 150                 155                 160
Lys Ser Gly Asp Arg Ser Gly Tyr Ser Ser Pro Gly Ser Pro Gly Thr
                165                 170                 175
Pro Gly Ser Arg Ser Arg Thr Pro Ser Leu Pro Thr Pro Pro Thr Arg
            180                 185                 190
Glu Pro Lys Lys Val Ala Val Val Arg Thr Pro Pro Lys Ser Pro Ser
        195                 200                 205
```

-continued

```
Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 5
<211> LENGTH: 758
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175
```

```
Asp Thr Glu Gly Gly Arg His Ala Pro Glu Leu Leu Lys His Gln Leu
            180                 185                 190

Leu Gly Asp Leu His Gln Gly Pro Pro Leu Lys Gly Ala Gly Gly
        195                 200                 205

Lys Glu Arg Pro Gly Ser Lys Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
        260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590
```

```
Gln Ile Ile Asn Lys Lys Leu Asp Leu Ser Asn Val Gln Ser Lys Cys
        595                 600                 605
Gly Ser Lys Asp Asn Ile Lys His Val Pro Gly Gly Ser Val Gln
610                 615                 620
Ile Val Tyr Lys Pro Val Asp Leu Ser Lys Val Thr Ser Lys Cys Gly
625                 630                 635                 640
Ser Leu Gly Asn Ile His His Lys Pro Gly Gly Gln Val Glu Val
                645                 650                 655
Lys Ser Glu Lys Leu Asp Phe Lys Asp Arg Val Gln Ser Lys Ile Gly
                660                 665                 670
Ser Leu Asp Asn Ile Thr His Val Pro Gly Gly Asn Lys Lys Ile
                675                 680                 685
Glu Thr His Lys Leu Thr Phe Arg Glu Asn Ala Lys Ala Lys Thr Asp
        690                 695                 700
His Gly Ala Glu Ile Val Tyr Lys Ser Pro Val Val Ser Gly Asp Thr
705                 710                 715                 720
Ser Pro Arg His Leu Ser Asn Val Ser Ser Thr Gly Ser Ile Asp Met
                725                 730                 735
Val Asp Ser Pro Gln Leu Ala Thr Leu Ala Asp Glu Val Ser Ala Ser
                740                 745                 750
Leu Ala Lys Gln Gly Leu
        755

<210> SEQ ID NO 6
<211> LENGTH: 776
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Ala Gln Pro His Thr Glu
                85                  90                  95
Ile Pro Glu Gly Thr Thr Ala Glu Glu Ala Gly Ile Gly Asp Thr Pro
                100                 105                 110
Ser Leu Glu Asp Glu Ala Ala Gly His Val Thr Gln Glu Pro Glu Ser
        115                 120                 125
Gly Lys Val Val Gln Glu Gly Phe Leu Arg Glu Pro Gly Pro Pro Gly
    130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro Ser Gly Thr Gly Pro Glu
                165                 170                 175
Asp Thr Glu Gly Gly Arg His Ala Pro Glu Leu Leu Lys His Gln Leu
                180                 185                 190
Leu Gly Asp Leu His Gln Glu Gly Pro Pro Leu Lys Gly Ala Gly Gly
        195                 200                 205
```

```
Lys Glu Arg Pro Gly Ser Lys Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Ala Thr Lys Gln Val Gln Arg Arg Pro Pro
            500                 505                 510

Pro Ala Gly Pro Arg Ser Glu Arg Gly Glu Pro Pro Lys Ser Gly Asp
        515                 520                 525

Arg Ser Gly Tyr Ser Ser Pro Gly Ser Pro Gly Thr Pro Gly Ser Arg
    530                 535                 540

Ser Arg Thr Pro Ser Leu Pro Thr Pro Pro Thr Arg Glu Pro Lys Lys
545                 550                 555                 560

Val Ala Val Val Arg Thr Pro Pro Lys Ser Pro Ser Ser Ala Lys Ser
                565                 570                 575

Arg Leu Gln Thr Ala Pro Val Pro Met Pro Asp Leu Lys Asn Val Lys
            580                 585                 590

Ser Lys Ile Gly Ser Thr Glu Asn Leu Lys His Gln Pro Gly Gly Gly
        595                 600                 605

Lys Val Gln Ile Ile Asn Lys Lys Leu Asp Leu Ser Asn Val Gln Ser
    610                 615                 620
```

-continued

```
Lys Cys Gly Ser Lys Asp Asn Ile Lys His Val Pro Gly Gly Gly Ser
625                 630                 635                 640

Val Gln Ile Val Tyr Lys Pro Val Asp Leu Ser Lys Val Thr Ser Lys
            645                 650                 655

Cys Gly Ser Leu Gly Asn Ile His His Lys Pro Gly Gly Gly Gln Val
                660                 665                 670

Glu Val Lys Ser Glu Lys Leu Asp Phe Lys Asp Arg Val Gln Ser Lys
            675                 680                 685

Ile Gly Ser Leu Asp Asn Ile Thr His Val Pro Gly Gly Gly Asn Lys
            690                 695                 700

Lys Ile Glu Thr His Lys Leu Thr Phe Arg Glu Asn Ala Lys Ala Lys
705                 710                 715                 720

Thr Asp His Gly Ala Glu Ile Val Tyr Lys Ser Pro Val Val Ser Gly
                725                 730                 735

Asp Thr Ser Pro Arg His Leu Ser Asn Val Ser Ser Thr Gly Ser Ile
                740                 745                 750

Asp Met Val Asp Ser Pro Gln Leu Ala Thr Leu Ala Asp Glu Val Ser
            755                 760                 765

Ala Ser Leu Ala Lys Gln Gly Leu
            770                 775

<210> SEQ ID NO 7
<211> LENGTH: 432
<212> TYPE: PRT
<213> ORGANISM: Rattus norvegicus

<400> SEQUENCE: 7

Met Ala Glu Pro Arg Gln Glu Phe Asp Thr Met Glu Asp Gln Ala Gly
1               5                   10                  15

Asp Tyr Thr Met Leu Gln Asp Gln Glu Gly Asp Met Asp His Gly Leu
                20                  25                  30

Lys Glu Ser Pro Pro Gln Pro Pro Ala Asp Asp Gly Ser Glu Glu Pro
            35                  40                  45

Gly Ser Glu Thr Ser Asp Ala Lys Ser Thr Pro Thr Ala Glu Asp Val
50                  55                  60

Thr Ala Pro Leu Val Glu Glu Arg Ala Pro Asp Lys Gln Ala Thr Ala
65                  70                  75                  80

Gln Ser His Thr Glu Ile Pro Glu Gly Thr Thr Ala Glu Glu Ala Gly
                85                  90                  95

Ile Gly Asp Thr Pro Asn Met Glu Asp Gln Ala Ala Gly His Val Thr
                100                 105                 110

Gln Ala Arg Val Ala Gly Val Ser Lys Asp Arg Thr Gly Asn Asp Glu
            115                 120                 125

Lys Lys Ala Lys Gly Ala Asp Gly Lys Thr Gly Lys Ile Ala Thr
            130                 135                 140

Pro Arg Gly Ala Ala Thr Pro Gly Gln Lys Gly Thr Ser Asn Ala Thr
145                 150                 155                 160

Arg Ile Pro Ala Lys Thr Thr Pro Ser Pro Lys Thr Pro Pro Gly Ser
                165                 170                 175

Gly Glu Pro Pro Lys Ser Gly Glu Arg Ser Gly Tyr Ser Ser Pro Gly
            180                 185                 190

Ser Pro Gly Thr Pro Gly Ser Arg Ser Arg Thr Pro Ser Leu Pro Thr
            195                 200                 205

Pro Pro Thr Arg Glu Pro Lys Lys Val Ala Val Val Arg Thr Pro Pro
210                 215                 220
```

```
Lys Ser Pro Ser Ala Ser Lys Ser Arg Leu Gln Thr Ala Pro Val Pro
225                 230                 235                 240

Met Pro Asp Leu Lys Asn Val Arg Ser Lys Ile Gly Ser Thr Glu Asn
                245                 250                 255

Leu Lys His Gln Pro Gly Gly Lys Val Gln Ile Ile Asn Lys Lys
            260                 265                 270

Leu Asp Leu Ser Asn Val Gln Ser Lys Cys Gly Ser Lys Asp Asn Ile
            275                 280                 285

Lys His Val Pro Gly Gly Ser Val Gln Ile Val Tyr Lys Pro Val
        290                 295                 300

Asp Leu Ser Lys Val Thr Ser Lys Cys Gly Ser Leu Gly Asn Ile His
305                 310                 315                 320

His Lys Pro Gly Gly Gly Gln Val Glu Val Lys Ser Glu Lys Leu Asp
                325                 330                 335

Phe Lys Asp Arg Val Gln Ser Lys Ile Gly Ser Leu Asp Asn Ile Thr
                340                 345                 350

His Val Pro Gly Gly Gly Asn Lys Lys Ile Glu Thr His Lys Leu Thr
            355                 360                 365

Phe Arg Glu Asn Ala Lys Ala Lys Thr Asp His Gly Ala Glu Ile Val
370                 375                 380

Tyr Lys Ser Pro Val Val Ser Gly Asp Thr Ser Pro Arg His Leu Ser
385                 390                 395                 400

Asn Val Ser Ser Thr Gly Ser Ile Asp Met Val Asp Ser Pro Gln Leu
            405                 410                 415

Ala Thr Leu Ala Asp Glu Val Ser Ala Ser Leu Ala Lys Gln Gly Leu
            420                 425                 430

<210> SEQ ID NO 8
<211> LENGTH: 430
<212> TYPE: PRT
<213> ORGANISM: Mus musculus

<400> SEQUENCE: 8

Met Ala Asp Pro Arg Gln Glu Phe Asp Thr Met Glu Asp His Ala Gly
1               5                   10                  15

Asp Tyr Thr Leu Leu Gln Asp Gln Glu Gly Asp Met Asp His Gly Leu
            20                  25                  30

Lys Glu Ser Pro Pro Gln Pro Pro Ala Asp Asp Gly Ala Glu Glu Pro
            35                  40                  45

Gly Ser Glu Thr Ser Asp Ala Lys Ser Thr Pro Thr Ala Glu Asp Val
50                  55                  60

Thr Ala Pro Leu Val Asp Glu Arg Ala Pro Asp Lys Gln Ala Ala Ala
65                  70                  75                  80

Gln Pro His Thr Glu Ile Pro Glu Gly Ile Thr Ala Glu Glu Ala Gly
                85                  90                  95

Ile Gly Asp Thr Pro Asn Gln Glu Asp Gln Ala Ala Gly His Val Thr
            100                 105                 110

Gln Ala Arg Val Ala Ser Lys Asp Arg Thr Gly Asn Asp Glu Lys Lys
        115                 120                 125

Ala Lys Gly Ala Asp Gly Lys Thr Gly Ala Lys Ile Ala Thr Pro Arg
130                 135                 140

Gly Ala Ala Ser Pro Ala Gln Lys Gly Thr Ser Asn Ala Thr Arg Ile
145                 150                 155                 160

Pro Ala Lys Thr Thr Pro Ser Pro Lys Thr Pro Pro Gly Ser Gly Glu
```

```
                   165                 170                 175
Pro Pro Lys Ser Gly Glu Arg Ser Gly Tyr Ser Ser Pro Gly Ser Pro
            180                 185                 190

Gly Thr Pro Gly Ser Arg Ser Arg Thr Pro Ser Leu Pro Thr Pro Pro
        195                 200                 205

Thr Arg Glu Pro Lys Lys Val Ala Val Val Arg Thr Pro Pro Lys Ser
    210                 215                 220

Pro Ser Ala Ser Lys Ser Arg Leu Gln Thr Ala Pro Val Pro Met Pro
225                 230                 235                 240

Asp Leu Lys Asn Val Arg Ser Lys Ile Gly Ser Thr Glu Asn Leu Lys
                245                 250                 255

His Gln Pro Gly Gly Gly Lys Val Gln Ile Ile Asn Lys Lys Leu Asp
            260                 265                 270

Leu Ser Asn Val Gln Ser Lys Cys Gly Ser Lys Asp Asn Ile Lys His
                275                 280                 285

Val Pro Gly Gly Gly Ser Val Gln Ile Val Tyr Lys Pro Val Asp Leu
        290                 295                 300

Ser Lys Val Thr Ser Lys Cys Gly Ser Leu Gly Asn Ile His His Lys
305                 310                 315                 320

Pro Gly Gly Gly Gln Val Glu Val Lys Ser Glu Lys Leu Asp Phe Lys
                325                 330                 335

Asp Arg Val Gln Ser Lys Ile Gly Ser Leu Asp Asn Ile Thr His Val
            340                 345                 350

Pro Gly Gly Gly Asn Lys Lys Ile Glu Thr His Lys Leu Thr Phe Arg
        355                 360                 365

Glu Asn Ala Lys Ala Lys Thr Asp His Gly Ala Glu Ile Val Tyr Lys
    370                 375                 380

Ser Pro Val Val Ser Gly Asp Thr Ser Pro Arg His Leu Ser Asn Val
385                 390                 395                 400

Ser Ser Thr Gly Ser Ile Asp Met Val Asp Ser Pro Gln Leu Ala Thr
                405                 410                 415

Leu Ala Asp Glu Val Ser Ala Ser Leu Ala Lys Gln Gly Leu
            420                 425                 430
```

METHODS FOR TREATING TAUOPATHY

CROSS-REFERENCE

This application is a 35 U.S.C. § 371 national stage entry of International Application No. PCT/US2016/013700, filed Jan. 15, 2016, which application claims the benefit of U.S. Provisional Patent Application No. 62/104,645, filed Jan. 16, 2015, which applications are incorporated herein by reference in their entireties.

INTRODUCTION

The microtubule-binding protein tau is expressed in the central nervous system and plays a critical role in the neuronal architecture by stabilizing the intracellular microtubule network. Tau is a major component of neurofibrillary inclusions characteristic of Alzheimer's disease (AD) and other neurodegenerative tauopathies. Altered forms of tau, such as acetylated tau, have been detected in AD and other tauopathies.

SUMMARY

The present disclosure provides methods of reducing the level of acetylated Tau in a neuron or a glial cell in an individual, the methods involving administering to the individual a prodrug that is converted in the individual to salicylate. The present disclosure provides methods of treating a tauopathy in an individual, the methods involving administering to the individual a prodrug that is converted in the individual to salicylate.

BRIEF DESCRIPTION OF THE DRAWINGS

FIGS. 1A-1D depict the effect of salicylate on the level of acetylated tau in cells in vitro.

FIGS. 2A and 2B depict the effect of a K174Q mutation on acetylated tau-lowering effects of salicylate.

FIGS. 4A-4C depict the effect of salsalate on neuronal loss in the hippocampus.

FIGS. 6A-6D depict an amino acid sequence alignment of human Tau isoform amino acid sequences. *Homo sapiens* Tau isoform 2 (SEQ ID NO: 1); *Homo sapiens* Tau isoform 3 (SEQ ID NO:2); *Homo sapiens* Tau isoform 4 (SEQ ID NO:3); *Homo sapiens* Tau isoform 5 (SEQ ID NO:4); *Homo sapiens* Tau isoform 1 (SEQ ID NO:5); and *Homo sapiens* Tau isoform 6 (SEQ ID NO:6).

FIG. 7 depicts an amino acid sequence alignment of human Tau isoform 2 (SEQ ID NO: 1), rat Tau (SEQ ID NO:7), and mouse Tau (SEQ ID NO:8).

FIGS. 12A and 12B provide silver staining results in neurites from neocortex and hippocampal regions for mice treated with SSA. Analysis of NFTs by Gallyas silver staining (FIG. 12A) and quantification of silver-positive cells in neurites from neocortex and hippocampal regions CA1 and CA3 (FIG. 12B) in vehicle-treated NTG mice and PS19 mice treated with vehicle or SSA. Scale bar, 250 µm (c, top); 25 µm (c, middle and bottom); n=8 mice (age 10-11 months) per genotype per treatment; *P<0.05, unpaired Student's t-test. Values are mean±s.e.m.

DEFINITIONS

Figure 3A:
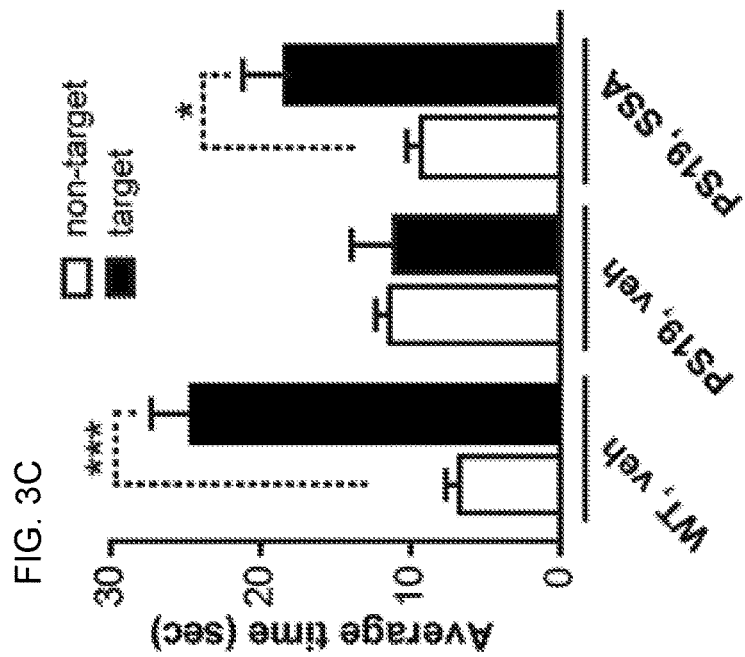
FIGS. 3A-3C depict the effect of salsalate on spatial memory in vivo.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The term "effective amount" or "therapeutically effective amount" means a dosage sufficient to provide for treatment for the disease state being treated or to otherwise provide the desired effect (e.g., induction of an effective immune response, reduction of chronic immune hyperactivity, etc.). The precise dosage will vary according to a variety of factors such as subject-dependent variables (e.g., weight, age, etc.), the disease, and the treatment being effected.

The terms "individual," "host," "subject," and "patient," used interchangeably herein, refer to a mammal, including, but not limited to, murines, lagomorphs, non-human primates, humans, etc. In some embodiments, an individual is a human. In some embodiments, an individual is a rodent (e.g., a mouse, a rat, etc.) or a lagomorph.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3-$), ethyl ($CH_3CH_2-$), n-propyl ($CH_3CH_2CH_2-$), isopropyl (($CH_3)_2CH-$), n-butyl ($CH_3CH_2CH_2CH_2-$), isobutyl (($CH_3)_2$ CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —$N_3$.

"Carboxyl," "carboxy" or "carboxylate" refers to —$CO_2H$ or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O—alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO— heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

"Nitro" refers to the group —NO2.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cycloalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cycloalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —$SO_2R^{70}$, —$SO_2O^-M^+$, —$SO_2R^{70}$, —$OSO_2R^{70}$, —$OSO_2O^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{80}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

As used herein, a "pharmaceutical composition" is meant to encompass a composition suitable for administration to a subject, such as a mammal, e.g., a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a prodrug" includes a plurality of such prodrugs and reference to "the salsalate compound" includes reference to one or more salsalate compounds and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of reducing the level of acetylated Tau in a neuron or a glial cell in an individual, the methods involving administering to the individual a prodrug that is converted in the individual to salicylate.

The present disclosure provides a method for reducing the level of an acetylated Tau (Ac-Tau) polypeptide in a cell (e.g., a cell that normally produces Tau, e.g., a neuron or a glial cell) in an individual. The method generally involves administering to the individual an effective amount of a prodrug that is converted in the individual to salicylate. In some cases, salicylate is conjugated to a moiety that facilitates crossing the blood-brain barrier (BBB). Reducing the level of an acetylated Tau (Ac-Tau) polypeptide in a cell (e.g., a cell that normally produces Tau, e.g., a neuron or a glial cell) in an individual can treat a tauopathy. Thus, the present disclosure provides methods of treating a tauopathy in an individual, the method generally involving administering to the individual an effective amount of a prodrug that is converted in the individual to salicylate.

Tau amino acid sequences are known in the art. See, e.g., the amino acid sequences found under the GenBank accession numbers in parentheses in the following: Human Tau transcript variant 1 mRNA (NM_016835.3) and isoform 1 protein (NP_058519.2); human Tau transcript variant 2 mRNA (NM_005910.4) and isoform 2 protein (NP_005901.2); human Tau transcript variant 3 mRNA (NM_016834.3) and isoform 3 protein (NP_058518.1); human Tau transcript variant 4 mRNA (NM_016841.3) and isoform 4 protein (NP_058525.1); human Tau transcript variant 5 mRNA (NM_001123067.2) and isoform 5 protein (NP_001116539.1); and human Tau transcript variant 6 mRNA (NM_001123066.2) and isoform 6 protein (NP_001116538.1).

Exemplary Tau amino acid sequences are depicted in FIGS. 6A-D (SEQ ID NOs: 1-6, respectively), where the sequences in FIGS. 6A-D are: *Homo sapiens* Tau isoform 2 (GenBank Accession No. NP_005901; SEQ ID NO: 1); *Homo sapiens* Tau isoform 3 (GenBank Accession No. NP_058518; SEQ ID NO:2); *Homo sapiens* Tau isoform 4 (GenBank Accession No. NP_058525; SEQ ID NO:3); *Homo sapiens* Tau isoform 5 (GenBank Accession No. NP_001116539; SEQ ID NO:4); *Homo sapiens* Tau isoform 1 (GenBank Accession No. NP_058519; SEQ ID NO:5); and *Homo sapiens* Tau isoform 6 (GenBank Accession No. NP_001116538; SEQ ID NO:6). The amino acid sequences set forth in SEQ ID NOs: 1-6 are aligned in FIGS. 6A-D.

FIG. 7 depicts an amino acid sequence alignment of human Tau isoform 2 (SEQ ID NO: 1), rat Tau (SEQ ID NO:7), and mouse Tau (SEQ ID NO:8).

A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of about 350 amino acids of any one of the amino acid sequences set forth in SEQ ID NOs: 1-6. A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to 383 amino acids of the amino acid sequence set forth in SEQ ID NO:2 (*Homo sapiens* Tau isoform 3). A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 412 amino acids of the amino acid sequence set forth in SEQ ID NO:4 (*Homo sapiens* Tau isoform 5). A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, or from about 400 amino acids to about 441 amino acids, of the amino acid sequence set forth in SEQ ID NO: 1 (*Homo sapiens* Tau isoform 2). A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, from about 400 amino acids to about 500 amino acids, from about 500 amino acids to about 600 amino acids, from about 600 amino acids to about 700 amino acids, or from about 700 amino acids to about 758 amino acids, of the amino acid sequence set forth in SEQ ID NO:5 (*Homo sapiens* Tau isoform 1). A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, from about 400 amino acids to about 500 amino acids, from about 500 amino acids to about 600 amino acids, from about 600 amino acids to about 700 amino acids, or from about 700 amino acids to about 776 amino acids, of the amino acid sequence set forth in SEQ ID NO:6 (*Homo sapiens* Tau isoform 6).

Possible phosphorylation sites of a Tau isoform 2 polypeptide (e.g., as depicted in FIG. 1B and as set forth in SEQ ID NO: 1) include the following amino acids: 46, 50, 69, 111, 123, 153, 175, 181, 195, 198, 199, 202, 205, 208, 210, 212, 214, 217, 231, 235, 237, 238, 258, 262, 293, 305, 320, 324, 352, 356, 373, 394, 396, 400, 404, 409, 412, 413, 416, and 422. For example, one or more of serine residues 46, 199, 202, 235, 262, 396, 404, and 422 and/or one or more of threonine residues 50, 69, 111, 153, 175, 181, 205, 212, 217, and 231 of a Tau polypeptide can be phosphorylated. Corresponding phosphorylation sites in other Tau polypeptides can be readily determined experimentally, or by examining the amino acid sequence alignment presented in FIGS. 6A-D and FIG. 7.

A Tau polypeptide can have a length of from about 350 amino acids to about 780 amino acids, e.g., from about 350 amino acids to about 385 amino acids, from about 385 amino acids to about 415 amino acids, from about 415 amino acids to about 445 amino acids, from about 445 amino acids to about 760 amino acids, or from about 760 amino acids to about 780 amino acids. In some embodiments, a Tau polypeptide has a length of 352 amino acids, 383 amino acids, 412 amino acids, 441 amino acids, 758 amino acids, or 776 amino acids.

A number of Lysine (Lys) residues on a Tau polypeptide can be acetylated. For example, a Tau isoform 2 can be acetylated at one or more amino acids, including but not limited to, Lys-163, Lys-174, Lys-180, Lys-190, Lys-267, Lys-274, Lys-281, Lys-369, and Lys-385 (e.g., of the amino acid sequence depicted in FIG. 1B and as set forth in SEQ ID NO: 1). Corresponding acetylation sites in other Tau polypeptides can be readily determined experimentally (e.g., as described in the Examples), or by examining the amino acid sequence alignment presented in FIGS. 6A-D. For example, as shown in FIGS. 6A-D, Lys-163 of Tau isoform 2 corresponds to amino acid 105 of Tau isoform 3, amino acid 105 of Tau isoform 4, amino acid 134 of Tau isoform 5, amino acid 480 of Tau isoform 6, and amino acid 480 of Tau isoform 1.

In some embodiments, an acetylated Tau polypeptide is acetylated at two, three, four, five, six, seven, eight, or nine of Lys-163, Lys-174, Lys-180, Lys-190, Lys-267, Lys-274, Lys-281, Lys-369, and Lys-385 of a Tau isoform 2 polypeptide or corresponding lysine residues in a different Tau isoform. In some embodiments, an acetylated Tau polypeptide comprises acetylated Lys-163, acetylated Lys-174, and acetylated Lys-190 of a Tau isoform 2 polypeptide or corresponding lysine residues in a different Tau isoform. In some embodiments, an acetylated Tau polypeptide comprises acetylated Lys-163, acetylated Lys-174, acetylated Lys-180, acetylated Lys-190, acetylated Lys-267, acetylated Lys 274, acetylated Lys-281, acetylated Lys-369, and acetylated Lys-385 of a Tau isoform 2 polypeptide or corresponding lysine residues in a different Tau isoform.

In some cases, an effective amount of a prodrug that is converted in an individual to salicylic acid is an amount that decreases the level of acetylated Tau polypeptide in a cell that normally produces Tau (e.g., a neuronal cell; a glial cell) by at least about 10%, at least about 15%, at least about 20%, at least about 25%, at least about 30%, at least about 35%, at least about 40%, at least about 45%, at least about 50%, at least about 60%, at least about 70%, at least about 80%, or more than 80%, compared to the level of acetylated Tau polypeptide in the cell before treatment with the prodrug or in the absence of treatment with the prodrug.

A decrease in the level of acetylated Tau polypeptide in a cell (e.g., in a cell that normally produces Tau, such as a neuron or a glial cell) can result in a decrease in the level of phosphorylated Tau and/or a decrease in the level of total Tau. Thus, in some cases, an effective amount of a prodrug that is converted in an individual to salicylic acid is an amount that decreases the level of acetylated Tau polypeptide in a cell (e.g., in a cell that normally produces Tau, such as a neuron or a glial cell) and also decreases the level of phosphorylated Tau polypeptide in the cell. In some cases, an effective amount of a prodrug that is converted in an individual to salicylic acid is an amount that decreases the level of acetylated Tau polypeptide in a cell that normally produces Tau (e.g., a neuronal cell; a glial cell) and in some embodiments reduces the level of phosphorylated Tau in the cell by at least about 10%, at least about 15%, at least about 20%, at least about 25%, at least about 30%, at least about 35%, at least about 40%, at least about 45%, at least about 50%, at least about 60%, at least about 70%, at least about 80%, or more than 80%, compared to the level of phosphorylated Tau in the cell before treatment with the prodrug or in the absence of treatment with the prodrug.

A decrease in the level of acetylated Tau polypeptide in a cell (e.g., in a cell that normally produces Tau, such as a neuron or a glial cell) can result in a decrease in total Tau levels. Thus, in some embodiments, a prodrug that decreases the level of acetylated Tau polypeptide in a cell (e.g., in a cell that normally produces Tau, such as a neuron or a glial cell) also decreases the level of total Tau polypeptide in the cell. In some cases, an effective amount of prodrug that is converted in an individual to salicylic acid is an amount that reduces the level of total Tau in the cell by at least about 10%, at least about 15%, at least about 20%, at least about 25%, at least about 30%, at least about 35%, at least about 40%, at least about 45%, at least about 50%, at least about 60%, at least about 70%, at least about 80%, or more than 80%, compared to the level of total Tau in the cell in the absence of treatment with the prodrug, or before treatment with the prodrug.

A decrease in the level of acetylated Tau polypeptide in a cell (e.g., in a cell that normally produces Tau, such as a neuron or a glial cell) can result in an increase in a biological activity of a Tau polypeptide. Thus, in some embodiments, a prodrug that decreases the level of acetylated Tau polypeptide in a cell (e.g., in a cell that normally produces Tau, such as a neuron or a glial cell) also increases a biological activity of Tau polypeptide in the cell. In some cases, an effective amount of prodrug that is converted in an individual to salicylic acid is an amount that increases the level of active Tau polypeptide in the cell by at least about 10%, at least about 15%, at least about 20%, at least about 25%, at least about 30%, at least about 35%, at least about 40%, at least about 45%, at least about 50%, at least about 60%, at least about 70%, at least about 80%, at least about 2-fold, at least about 2.5-fold, at least about 3-fold, at least about 5-fold, at least about 7-fold, at least about 10-fold, or more than 10-fold, compared to the level of active Tau polypeptide in the cell in the absence of the agent. Tau biological activity includes, e.g., stabilization of microtubules.

Prodrugs

In some cases, a prodrug suitable for use in a subject method is a compound of Formula I:

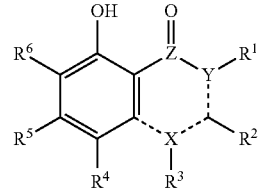

(Formula I)

where X is optionally present, and where X, Y, and Z are each independently CH, $CH_2$, N, O, S, alkyl, substituted alkyl, aryl, or substituted aryl; a halogen, an amine group, a substituted or unsubstituted unbranched $C_1$-$C_{12}$ acyclic aliphatic group, a substituted or unsubstituted branched $C_1$-$C_{12}$ acyclic aliphatic group, a substituted or unsubstituted $C_3$-$C_8$ cycloalkyl group, a substituted or unsubstituted $C_3$-$C_8$ cycloalkenyl group, a fluorinated $C_1$-$C_{12}$ alkyl group, a substituted or unsubstituted aryl group, a substituted or unsubstituted heterocycle, a substituted or unsubstituted $C_1$-$C_{12}$ alkoxy group, a fluorinated $C_1$-$C_{12}$ alkoxy group, a hydroxyl group, a nitrile group, an azide group, a nitro group, an acyl group, or a thiol group;

and each of $R^1$, $R^2$, $R^3$, $R^4$, $R^5$, and $R^6$ is independently hydrogen, alkyl, substituted alkyl, aryl, or substituted aryl; a halogen, an amine group, a substituted or unsubstituted unbranched $C_1$-$C_{12}$ acyclic aliphatic group, a substituted or unsubstituted branched $C_1$-$C_{12}$ acyclic aliphatic group, a substituted or unsubstituted $C_3$-$C_8$ cycloalkyl group, a substituted or unsubstituted $C_3$-$C_8$ cycloalkenyl group, a fluorinated $C_1$-$C_{12}$ alkyl group, a substituted or unsubstituted aryl group, a substituted or unsubstituted heterocycle, a substituted or unsubstituted $C_1$-$C_{12}$ alkoxy group, a fluorinated $C_1$-$C_{12}$ alkoxy group, a hydroxyl group, a nitrile group, an azide group, a nitro group, an acyl group, or a thiol group.

In some cases, $R^4$, $R^5$, and $R^6$ are each hydrogen. In some cases, $R^4$, $R^5$, and $R^6$ are each hydrogen; X is not present; Z is C; and Y is O. In some cases, $R^4$, $R^5$, and $R^6$ are each hydrogen; X is not present; Z is C; and Y is O; and $R^1$ is an alkyl, a substituted alkyl, an aryl, or a substituted aryl.

Prodrugs that are suitable for use in a subject method include, e.g., salsalate; a dimer of salicylic acid; conjugates of salicylic acid; and the like.

Prodrugs that are suitable for use in a subject method include, e.g.:

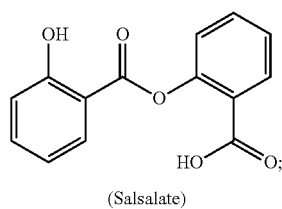

(Salsalate)

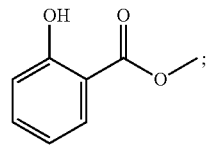

(SA1)

(SA2) 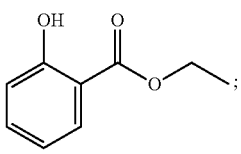

(SA3) 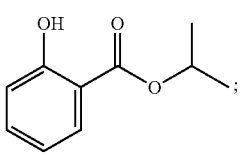

(SA4) 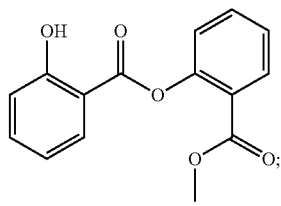

(SA5) 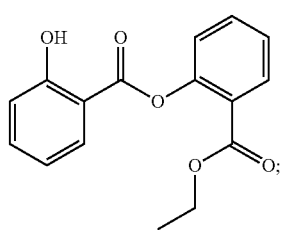

(SA6) 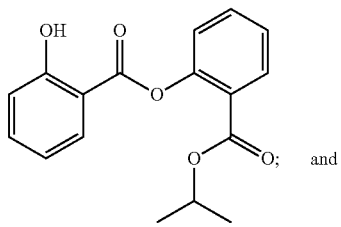

(SA7) 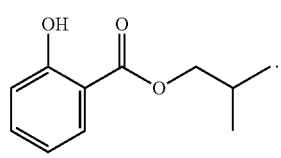

In some cases, the prodrug is salsalate:

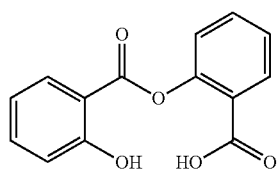 [SMILES: O=C(Oc1ccccc1C(=O)O)c1ccccc1O]

In some cases, the prodrug is disalicylide:

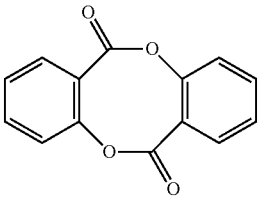

Disalicylide
CAS# 486-58-8

Enzymatic hydrolysis of disalicylide in vivo generates salicylic acid.

Conjugates

In some cases, the prodrug is a conjugate of salicylic acid, e.g., a conjugate comprising salicylic acid covalently linked to a moiety that facilitates crossing the BBB.

In some cases, the prodrug is a conjugate comprising salicylic acid covalently linked to a moiety that interacts with (e.g., binds to) an internalizing cell surface receptor. Suitable internalizing cell surface receptors include, e.g., a sialoglycoprotein receptor, an alpha(2,3)sialoglycoprotein receptor, a diphtheria toxin receptor a heparin-binding epidermal growth factor-like growth factor, a folate receptor, a glutamate receptor, a glutathione receptor, an insulin receptor, an insulin-like growth factor receptor, a leptin receptor, a low-density lipoprotein receptor, an LDL-related protein 1 receptor, an LRP2 receptor, an LRP4 receptor, an LRP5 receptor, an LRP6 receptor, an LRP8 receptor, a mannose 6-phosphate receptor, a scavenger receptor (class A or B, types I, II or III, or CD36 or CD163), a substance P receptor, a thiamine transporter, a transferrin-1 receptor, a transferrin-2 receptor, and a vitamin B12 receptor.

In some cases, the prodrug is a conjugate comprising salicylic acid covalently linked to a moiety that interacts with (e.g., binds to) a glucose transporter (GLUT-1). In some cases, the prodrug is a conjugate comprising salicylic acid covalently linked to a moiety that interacts with (e.g., binds to) a large amino acids transporter (LAT1). In some cases, the prodrug is a conjugate comprising salicylic acid covalently linked to a moiety that interacts with (e.g., binds to) a transporter at the blood-brain barrier, where such transporters include, but are not limited to, a lipid transporter and a low density lipoprotein receptor (LDLR). In some cases, the prodrug is a conjugate comprising salicylic acid covalently linked to a moiety that interacts with (e.g., binds to) a lipid transporter at the BBB. In some cases, the prodrug is a conjugate comprising salicylic acid covalently linked to a moiety that interacts with (e.g., binds to) an LDLR at the BBB.

In some cases, salicylic acid is conjugated to a sugar. In some cases, salicylic acid is conjugated to D-glucose. In some cases, salicylic acid is conjugated to an amino acid (e.g., phenylalanine). In some cases, salicylic acid is conjugated to a lysophosphatidylcholine. In some cases, salicylic acid is conjugated to an apolipoprotein.

Conjugates with a Sugar

In some cases, a suitable prodrug is a conjugate comprising salicylic acid covalently linked to a sugar. In some cases, the sugar is one that interacts with glucose transporter 1 (GLUT1), such that the prodrug is actively transported into the brain.

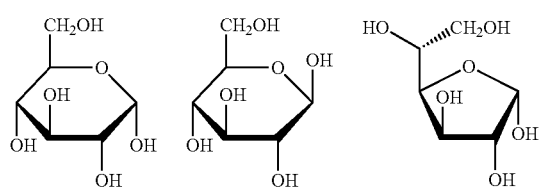

α-D-Glucopyranose   β-D-Glucopyranose   α-D-Glucofuranose

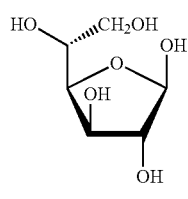

β-D-Glucofuranose

In some cases, the sugar is D-glucose. Thus, in some cases, the conjugate comprises salicylic acid covalently linked to D-glucose. In some cases, the salicylic acid is covalently linked to the D-glucose through the carboxylic acid of salicylic acid, generating glucosyl salicylate. In some cases, the salicylic acid is covalently linked to the D-glucose through the phenol of salicylic acid, generating salicylic acid glucoside. For example, in some cases, the conjugate is 2-O-β-D-glucopyranosyl salicylic acid.

Suitable conjugates include regioselectively glycosylated salicylic acid.

Examples of suitable conjugates comprising salicylic acid covalently linked to a sugar include:

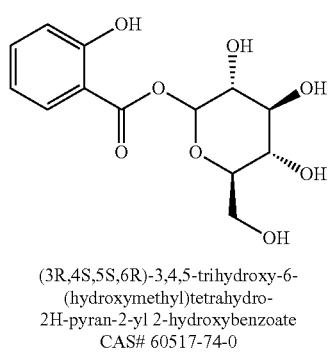

(3R,4S,5S,6R)-3,4,5-trihydroxy-6-
(hydroxymethyl)tetrahydro-
2H-pyran-2-yl 2-hydroxybenzoate
CAS# 60517-74-0

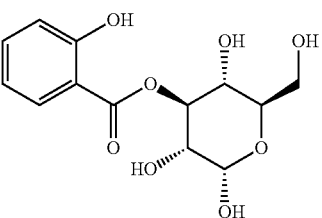

(2S,3R,4S,5S,6R)-2,3,5-trihydroxy-6-
(hydroxymethyl)tetrahydro-2H-pyran-4-yl
2-hydroxybenzoate
CAS# N/A

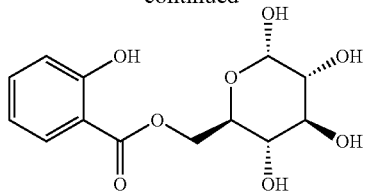

((2R,3S,4S,5R,6S)-3,4,5,6-
tetrahydroxytetrahydro-2H-pyran-2-yl)methyl
2-hydroxybenzoate
CAS# 16977-87-0

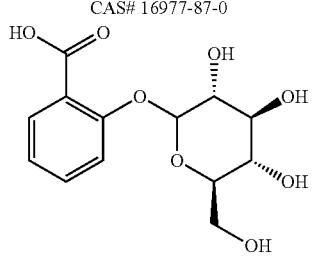

2-(((3R,4S,5S,6R)-3,4,5-trihydroxy-6-
(hydroxymethyl)tetrahydro-2H-
pyran-2-yl)oxy)benzoic acid
CAS# 6044-33-3

Formulations

In some cases, the prodrug is formulated with one or more agents that facilitate crossing the BBB. In some cases, the prodrug is chemically modified with a lipophilic agent. In some cases, the prodrug is encapsulated into a liposome. In some cases, the prodrug is conjugated to, or adsorbed onto, a nanoparticle.

Nanoparticles

In some cases, the prodrug is conjugated to, encapsulated within, or adsorbed onto, a nanoparticle that facilitates crossing the BBB. Suitable nanoparticles can comprise silica, lipid, carbohydrate, or other pharmaceutically acceptable polymers.

As used herein, a "nanoparticle" is a colloidal, polymeric, or elemental particle ranging in size from about 1 nm to about 1000 nm. Nanoparticles can be made up of silica, carbohydrate, lipid, or polymer molecules. Salicylic acid or a prodrug of salicylic acid can be either embedded in the nanoparticle matrix or may be adsorbed onto its surface. In one example, the nanoparticle may be made up of a biodegradable polymer such as poly(butylcyanoacrylate) (PBCA). Examples of elemental nanoparticles include carbon nanoparticles and iron oxide nanoparticles, which can then be coated with oleic acid (OA)-Pluronic. In this approach, a drug (e.g., salicylic acid or a prodrug of salicylic acid) is loaded into the nanoparticle, as described in Jain et al., Mol. Pharm. 2:194-205, 2005. Other nanoparticles are made of silica, and include those described, for example, in Burns et al., Nano Lett. 9:442-448, 2009.

Nanoparticles can be formed from any of a variety of polymers. Examples of suitable polymers include biodegradable polymers, such as poly(butyl cyanoacrylate), poly (lactide), poly(glycolide), poly-epsilon-caprolactone, poly (butylene succinate), poly(ethylene succinate), and poly(p-dioxanone); poly(ethyleneglycol); poly-2-hydroxyethylmethacrylate (poly(HEMA)); copolymers, such as poly(lactide-co-glycolide), poly(lactide)-poly(ethyleneglycol), poly(poly(ethyleneglycol)cyanoacrylate-co-hexadecylcyanoacrylate, and poly[HEMA-co-methacrylic acid]; proteins, such as fibrinogen, collagen, gelatin, and elastin; and polysaccharides, such as amylopectin, α-amylose, and chitosan.

In some cases, the prodrug is conjugated to, or adsorbed onto, a polyisohexylcyanoacrylate nanoparticle. In some cases, the prodrug is conjugated to, or adsorbed onto, a polysorbate 80-coated poly(butyl cyanoacrylate) nanoparticle. In some cases, the prodrug is conjugated to, or adsorbed onto, a polysorbate 80-coated nanoparticle.

Other suitable nanoparticles include solid lipid nanoparticles (SLN). SLN approaches are described, for example, in Kreuter, Ch. 24, In V. P. Torchilin (ed), Nanoparticles as Drug Carriers pp. 527-548, Imperial College Press, 2006). Examples of lipid molecules for solid lipid nanoparticles include stearic acid and modified stearic acid, such as stearic acid-PEG 2000; soybean lecithin; and emulsifying wax. Solid lipid nanoparticles can optionally include other components, including surfactants, such as Epicuron® 200, poloxamer 188 (Pluronic® F68), Brij 72, Brij 78, polysorbate 80 (Tween 80); and salts, such as taurocholate sodium.

Nanoparticles can also include nanometer-sized micelles. Micelles can be formed from any polymers described herein. Exemplary polymers for forming micelles include block copolymers, such as poly(ethylene glycol) and poly(epsilon-caprolactone). In one particular example, PEO-b-PCL block copolymer is synthesized via controlled ring-opening polymerization of epsilon-caprolactone by using an .alpha.-methoxy-to-hydroxy-poly(ethylene glycol) as a macroinitiator. To form micelles, the PEO-b-PCL block copolymers were dissolved in an organic solvent (e.g., tetrahydrofuran) and then deionized water was added to form a micellar solution. The organic solvent was evaporated to obtain nanometer-sized micelles.

Lipids

Lipid vectors can be formed using any biocompatible lipid or combination of lipids capable of forming lipid vectors (e.g., liposomes, micelles, and lipoplexes). Encapsulation of an agent (e.g., a prodrug of salicylic acid) into a lipid vector can protect the agent from damage or degradation or facilitate its entry into a cell. Lipid vectors, as a result of charge interactions (e.g., a cationic lipid vector and anionic cell membrane), interact and fuse with the cell membrane, thus releasing the agent into the cytoplasm. A liposome is a bilayered vesicle comprising one or more of lipid molecules, polypeptide-lipid conjugates, and lipid components. A lipoplex is a liposome formed with cationic lipid molecules to impart an overall positive charge to the liposome. A micelle is a vesicle with a single layer of surfactants or lipid molecules.

In certain embodiments, the lipid vector is a liposome. Typically, the lipids used are capable of forming a bilayer and are cationic. Classes of suitable lipid molecules include phospholipids (e.g., phosphatidylcholine), fatty acids, glycolipids, ceramides, glycerides, and cholesterols, or any combination thereof. Alternatively or in addition, the lipid vector can include neutral lipids (e.g., dioleoylphosphatidyl ethanolamine (DOPE)).

Examples of lipid molecules include natural lipids, such as cardiolipin (CL), phosphatidic acid (PA), phosphatidylcholine (PC), phosphatidylethanolamine (PE), phosphatidylglycerol (PG), phosphatidylinositol (PI), and phosphatidyl serine (PS); sphingolipids, such as sphingosine, ceramide, sphingomyelin, cerebrosides, sulfatides, gangliosides, and phytosphingosine; cationic lipids, such as 1,2-dioleoyl-3-trimethylammonium-propane (DOTAP), 1,2-dioleoyl-3-dimethylammonium-propane (DODAP), dimethyldioctadecyl ammonium bromide (DDAB), 3-.beta.-[N—(N',N'-dimethylaminoethane)carbamoly]cholesterol (DC-Chol), N-[1-(2,3,-ditetradecyloxy)propyl]-N,N-dimethyl-N-hydroxyethylammonium bromide (DMRIE), N-[1-(2,3,-dioleyloxy)propyl]-N,N-dimethyl-N-hydroxy ethylammonium bromide (DORIE), and 1,2-di-O-octadecenyl-3-trimethylammonium propane (DOTMA); phosphatidylcholines, such as 1,2-dilauroyl-sn-glycero-3-ethylphosphocholine, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), and 1-palmitoyl-2-oleoyl-sn-glycerol-3-phosphocholine (POPC); phosphoethanolamines, such as 1,2-dibutyryl-sn-glycero-3-phosphoethanolamine, 1,2-distearoyl-sn-glycero-3-phosphoethanolamine (DSPE), 1,2-dimyristoyl-sn-glycero-3-phosphoethanolamine (DMPE), 1,2-dipalmitoyl-sn-glycero-3-phosphoethanolamine (DPPE), 1,2-dioleoyl-sn-glycero-3-phosphoethanolamine (DOPE), and 1,2-dioleoyl-sn-glycero-3-phosphoethanolamine-N-(glutaryl); phosphatidic acids, such as 1,2-dimyristoyl-sn-glycero-3-phosphate, 1,2-dipalmitoyl-sn-glycero-3-phosphate, and 1,2-dioleoyl-sn-glycero-3-phosphate; phosphatidylglycerols, such as dipalmitoyl phosphatidylglycerol (DMPC), 1,2-dimyristoyl-sn-glycero-3-phospho-(1'-rac-glycerol), and 1,2-dioleoyl-sn-glycero-3-phospho-(1'-rac-glycerol); phosphatidylserines, such as 1,2-dimyristoyl-sn-glycero-3-phospho-L-serine, 1,2-dipalmitoyl-sn-glycero-3-phospho-L-serine, and 1,2-dioleoyl-sn-glycero-3-phospho-L-serine; cardiolipins, such as 1',3'-bis[1,2-d]myristoyl-sn-glycero-3-phospho]-sn-glycerol; and PEG-lipid conjugates, such as 1,2-dipalmitoyl-sn-glycero-3-phosphoethanolamine-N-[methoxy(polyethylene glycol)-750], 1,2-dipalmitoyl-sn-glycero-3-phosphoethanolamine-N-[methoxy(polyethylene glycol)-2000], 1,2-dipalmitoyl-sn-glycero-3-phosphoethanolamine-N-[methoxy(polyethylene glycol)-5000], 1,2-distearoyl-sn-glycero-3-phosphoethanolamine-N-[methoxy(polyethylene glycol)-2000], and 1,2-distearoyl-sn-glycero-3-phosphoethanolamine-N—[carboxy(polyethylene glycol)-2000].

Methods of Treating a Tauopathy

The present disclosure provides a method for treating a tauopathy in an individual. The method comprises administering to an individual in need thereof an effective amount of a prodrug that is converted in the individual to salicylate and that reduces the level of acetylated Tau in the cell, e.g., a prodrug that is converted in the individual to salicylate and that inhibits the acetyltransferase activity of an acetyltransferase that acetylates a Tau polypeptide.

Tauopathies are neurodegenerative diseases that are characterized, at least in part, by pathological aggregation of Tau protein, e.g., in neurofibrillary tangles. Examples of tauopathies include frontotemporal dementia, Alzheimer's disease, progressive supranuclear palsy, corticobasal degeneration, Down syndrome, dementia pugilistica, inclusion-body myositis, and frontotemporal lobar degeneration, also known as Pick's disease. Exemplary tauopathies include: diseases showing coexistence of tau and amyloid pathologies, e.g., Alzheimer's disease, Creutzfeldt-Jakob disease, dementia pugilistica, Down's syndrome, Gerstmann-Sträussler-Scheinker disease, inclusion body myositis, and prion protein cerebral amyloid angiopathy; diseases without distinct amyloid pathology, e.g., amyotrophic lateral sclerosis/Parkinsonism-dementia complex, argyrophilic grain dementia, corticobasal degeneration, diffuse neurofibrillary tangles with calcification, frontotemporal dementia with Parkinsonism linked to chromosome 17, Hallevorden-Spatz disease, multiple system atrophy, Niemann-Pick disease type C, Pick's disease, progressive subcortical gliosis, progressive supranuclear palsy, subacute sclerosing panencephalitis, and tangle-predominant Alzheimer's disease.

A subject method for treating a tauopathy in an individual generally involves administering an effective amount of a prodrug that is converted in the individual to salicylic acid and that inhibits acetylation of a Tau polypeptide in a cell that normally produces Tau (e.g., a neuronal cell and/or a glial cell) in the individual. In some embodiments, a subject method involves monotherapy, e.g., administration of an effective amount of a single active agent, e.g., an agent that inhibits acetylation of a Tau polypeptide in a cell that produces Tau (e.g., a neuronal cell and/or a glial cell). In some embodiments, a subject method involves monotherapy, e.g., administration of an effective amount of a single active agent, e.g., a prodrug that is converted in the individual to salicylic acid. In some embodiments, a subject method involves combination therapy, e.g., administration of a prodrug that is converted in the individual to salicylic acid and that inhibits acetylation of a Tau polypeptide in a cell (e.g., a neuron; a glial cell) is administered in combination therapy with one or more additional therapeutic agents.

An effective amount of a prodrug that is converted in the individual to salicylic acid and that inhibits acetylation of a Tau polypeptide in a cell that normally produces Tau (e.g., a neuronal cell and/or a glial cell) is an amount that is effective to ameliorate at least one symptom of a tauopathy, e.g., to alleviate an adverse symptom and/or to increase a normal function that was impaired as a result of the tauopathy. For example, in some embodiments, an effective amount of a prodrug that is converted in the individual to salicylic acid and that inhibits acetylation of a Tau polypeptide in a cell that normally produces Tau (e.g., a neuronal cell and/or a glial cell) is an amount that is effective to reduce the number of neurofibrillary lesions in the brain of an individual having a tauopathy. Where a subject method involves combination therapy, combined effective amounts of the active agents are amounts that, in combination, are effective to reduce the number of neurofibrillary lesions in the brain of an individual having a tauopathy. In some embodiments, an effective amount of an active agent is an amount that is effective to increase a cognitive function in the individual. Where a subject method involves combination therapy, combined effective amounts of the active agents are amounts that, in combination, are effective to increase a cognitive function in the individual.

Formulations, Dosages, and Routes of Administration

For simplicity, a prodrug that is converted in the individual to salicylic acid and that inhibits acetylation of a Tau polypeptide in a cell that normally produces Tau (e.g., a neuronal cell and/or a glial cell) is referred to below as an "active agent." An active agent can be incorporated into a variety of formulations for therapeutic administration. More particularly, an active agent can be formulated into pharmaceutical compositions by combination with appropriate pharmaceutically acceptable carriers or diluents, and may be formulated into preparations in solid, semi-solid, liquid or gaseous forms, such as, powders, granules, solutions, injections, inhalants, gels, hydrogels, microspheres, etc. As such, administration of an active agent can be achieved in various ways, including local, such as delivery into the affected tissue, oral, catheter mediated, intrathecal, buccal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In some embodiments, an active agent is formulated to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin. A BBB disrupting agent can be co-administered with an active agent when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to an active agent for use in the methods disclosed herein to facilitate transport across the epithelial wall of the blood vessel. Alternatively, drug delivery behind the BBB is by intrathecal delivery of therapeutics directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, phosphate buffered saline (PBS), Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see. Langer (1990) *Science* 249:1527-1533.

The pharmaceutical compositions can be administered for prophylactic and/or therapeutic treatments. Toxicity and therapeutic efficacy of the active agent can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active agent typically lies within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under Good Manufacturing Practice (GMP) conditions.

The effective amount of an active agent to be given to a particular patient will depend on a variety of factors, several of which will be different from patient to patient. A competent clinician will be able to determine an effective amount of an active agent to administer to a patient to treat a tauopathy. Utilizing LD50 animal data, and other information available for the inhibitor, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Formulations

In carrying out a subject treatment method (e.g., reducing the level of acetylated Tau polypeptide in a cell (e.g., a neuron; a glial cell) in an individual; treating a tauopathy), an active agent (a prodrug that is converted in the individual to salicylic acid and that inhibits acetylation of a Tau polypeptide in a cell that normally produces Tau (e.g., a neuronal cell and/or a glial cell)) may be administered to the host using any convenient means capable of resulting in the desired physiological effect (e.g., reduction in the level of acetylated Tau polypeptide in a neuronal cell and/or a glial cell in an individual; increase in cognitive function; reduction in neurofibrillary lesions; reduction in adverse effect of a tauopathy; etc.). Thus, the active agent can be incorporated into a variety of formulations for therapeutic administration. More particularly, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, an active agent(s) can be administered in the form of its (their) pharmaceutically acceptable salts, or the active agent may also be used alone or in appropriate association, as well as in combination, with other pharmaceutically active compounds. The following methods and excipients are merely exemplary and are in no way limiting.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying the active agent in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. The compounds of the present invention can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent calculated in an amount sufficient to produce the desired effect in association with a pharmaceutically acceptable diluent, carrier or vehicle. The specifications for a unit dosage form of an active agent depend on the particular active agent employed and the effect to be achieved, and the pharmacodynamics associated with each active agent in the host.

Other modes of administration will also find use with the subject invention. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations may also contain preservatives such as, but not limited to, chlorobutanol and benzalkonium chloride. A surfactant may be present to enhance absorption of an active agent by the nasal mucosa.

An active agent can be administered as injectables. Typically, injectable compositions are prepared as liquid solutions or suspensions; solid forms suitable for solution in, or suspension in, liquid vehicles prior to injection may also be prepared. The preparation may also be emulsified or the active agent encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the active agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Oral Formulations

In some embodiments, an active agent (a prodrug that is converted in the individual to salicylic acid and that inhibits acetylation of a Tau polypeptide in a cell that normally produces Tau (e.g., a neuronal cell and/or a glial cell) is formulated for oral delivery to an individual in need of such an agent.

For oral delivery, a formulation comprising an active agent will in some embodiments include an enteric-soluble coating material. Suitable enteric-soluble coating material include hydroxypropyl methylcellulose acetate succinate (HPMCAS), hydroxypropyl methyl cellulose phthalate (HP-MCP), cellulose acetate phthalate (CAP), polyvinyl phthalic acetate (PVPA), Eudragit™, and shellac.

As one non-limiting example of a suitable oral formulation, an active agent is formulated with one or more pharmaceutical excipients and coated with an enteric coating, as described in U.S. Pat. No. 6,346,269. For example, a solution comprising an active agent and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for an active agent include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include an active agent, formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) Biomaterials 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include an active agent formulated with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); Ring-Cap™ (Alza Corp.); Smartrix® (Smartrix Technologies, Inc.); SQZgel™ (MacroMed, Inc.); Geomatrix™ (Skye Pharma, Inc.); Oros® Tri-layer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Controlled Release Formulations

In some embodiments, an active agent (a prodrug that is converted in the individual to salicylic acid and that inhibits acetylation of a Tau polypeptide in a cell that normally produces Tau (e.g., a neuronal cell and/or a glial cell)) is formulated in a controlled release formulation.

Controlled release formulations suitable for use can be taken to mean any one of a number of extended release dosage forms. The following terms may be considered to be substantially equivalent to controlled release, for the purposes of the present disclosure: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, Extended-Release Dosage Forms, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable); and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems,* 1992 (Marcel Dekker, Inc.). Some of these formulations will now be discussed in more detail.

Enteric coatings are applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that function by virtue or the fact that their solubility in aqueous medium is pH-dependent, and they require conditions with a pH higher than normally encountered in the stomach.

One exemplary type of oral controlled release structure is enteric coating of a solid or liquid dosage form. The enteric coatings are designed to disintegrate in intestinal fluid for ready absorption. Delay of absorption of the active agent that is incorporated into a formulation with an enteric coating is dependent on the rate of transfer through the gastrointestinal tract, and so the rate of gastric emptying is an important factor. Some investigators have reported that a multiple-unit type dosage form, such as granules, may be superior to a single-unit type. Therefore, in one exemplary embodiment, an active agent may be contained in an enterically coated multiple-unit dosage form. In an exemplary embodiment, an active agent dosage form is prepared by spray-coating granules of an active agent-enteric coating agent solid dispersion on an inert core material. These granules can result in prolonged absorption of the drug with good bioavailability.

Typical enteric coating agents include, but are not limited to, hydroxypropylmethylcellulose phthalate, methacryclic acid-methacrylic acid ester copolymer, polyvinyl acetate-phthalate and cellulose acetate phthalate. Akihiko Hasegawa, *Application of solid dispersions of Nifedipine with enteric coating agent to prepare a sustained-release dosage form, Chem. Pharm. Bull.* 33: 1615-1619 (1985). Various enteric coating materials may be selected on the basis of testing to achieve an enteric coated dosage form designed ab initio to have an optimal combination of dissolution time, coating thicknesses and diametral crushing strength. S. C. Porter et al., *The Properties of Enteric Tablet Coatings Made From Polyvinyl Acetate-phthalate and Cellulose acetate Phthalate, J. Pharm. Pharmacol.* 22:42p (1970).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, *Super Saturation Mechanism of Drugs from Solid Dispersions with Enteric Coating Agents, Chem. Pharm. Bull.* 36: 4941-4950 (1998). The solid dispersions may be also called solid-state dispersions. The term "coprecipitates" may also be used to refer to those preparations obtained by the solvent methods.

The selection of the carrier may have an influence on the dissolution characteristics of the dispersed active agent because the dissolution rate of a component from a surface may be affected by other components in a multiple component mixture. For example, a water-soluble carrier may result in a fast release of the active agent from the matrix, or a poorly soluble or insoluble carrier may lead to a slower release of the active agent from the matrix. The solubility of the active agent may also be increased owing to some interaction with the carriers.

Examples of carriers useful in solid dispersions include, but are not limited to, water-soluble polymers such as polyethylene glycol, polyvinylpyrrolidone, and hydroxypropylmethyl—cellulose. Alternative carriers include phosphatidylcholine. Phosphatidylcholine is an amphoteric but water-insoluble lipid, which may improve the solubility of otherwise insoluble active agents in an amorphous state in phosphatidylcholine solid dispersions.

Other carriers include polyoxyethylene hydrogenated castor oil. Poorly water-soluble active agents may be included in a solid dispersion system with an enteric polymer such as hydroxypropylmethylcellulose phthalate and carboxymethylethylcellulose, and a non-enteric polymer, hydroxypropylmethylcellulose. Another solid dispersion dosage form includes incorporation of the active agent with ethyl cellulose and stearic acid in different ratios.

There are various methods commonly known for preparing solid dispersions. These include, but are not limited to, the melting method, the solvent method and the melting-solvent method.

Another controlled release dosage form is a complex between an ion exchange resin and an active agent. Ion exchange resin-drug complexes have been used to formulate sustained-release products of acidic and basic drugs. In one exemplary embodiment, a polymeric film coating is provided to the ion exchange resin-drug complex particles, making drug release from these particles diffusion controlled. See Y. Raghunathan et al., *Sustained-released drug delivery system I: Coded ion-exchange resin systems for phenylpropanolamine and other drugs, J. Pharm. Sciences* 70: 379-384 (1981).

Injectable microspheres are another controlled release dosage form. Injectable micro spheres may be prepared by non-aqueous phase separation techniques, and spray-drying techniques. Microspheres may be prepared using polylactic acid or copoly(lactic/glycolic acid). Shigeyuki Takada, *Utilization of an Amorphous Form of a Water-Soluble GPIIb/*

IIIa Antagonist for Controlled Release From Biodegradable Micro spheres, Pharm. Res. 14:1146-1150 (1997), and ethyl cellulose, Yoshiyuki Koida, Studies on Dissolution Mechanism of Drugs from Ethyl Cellulose Microcapsules, Chem. Pharm. Bull. 35:1538-1545 (1987).

Other controlled release technologies that may be used include, but are not limited to, SODAS (Spheroidal Oral Drug Absorption System), INDAS (Insoluble Drug Absorption System), IPDAS (Intestinal Protective Drug Absorption System), MODAS (Multiporous Oral Drug Absorption System), EFVAS (Effervescent Drug Absorption System), PRODAS (Programmable Oral Drug Absorption System), and DUREDAS (Dual Release Drug Absorption System) available from Elan Pharmaceutical Technologies. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant lipoate throughout the gastrointestinal tract. Controlled release characteristics of the individual beads may avoid high concentration of active agent being both released locally and absorbed systemically. The combination of both approaches serves to minimize the potential harm of the active agent with resultant benefits to patients.

IPDAS is composed of numerous high density controlled release beads. Each bead may be manufactured by a two step process that involves the initial production of a micromatrix with embedded active agent and the subsequent coating of this micromatrix with polymer solutions that form a rate-limiting semipermeable membrane in vivo. Once an IPDAS tablet is ingested, it may disintegrate and liberate the beads in the stomach. These beads may subsequently pass into the duodenum and along the gastrointestinal tract, e.g., in a controlled and gradual manner, independent of the feeding state. Release of the active agent occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, an immediate release granulate may be included in the tablet. The tablet may be broken prior to administration, without substantially compromising drug release, if a reduced dose is required for individual titration.

MODAS is a drug delivery system that may be used to control the absorption of water soluble agents. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients. This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug releasing pores of the tablet are distributed over substantially the entire surface of the tablet. This facilitates uniform drug absorption reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a microenvironment within the tablet that facilitates more predictable release and absorption rates. The addition of an immediate release outer coating may allow for development of combination products.

Additionally, PRODAS may be used to deliver an active agent. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain an active agent. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastroirritants where release can be delayed until the formulation reaches more distal regions of the gastrointestinal tract. One value of PRODAS technology lies in the inherent flexibility to formulation whereby combinations of mini tablets, each with different release rates, are incorporated into one dosage form. As well as potentially permitting controlled absorption over a specific period, this also may permit targeted delivery of drug to specific sites of absorption throughout the gastrointestinal tract. Combination products also may be possible using mini tablets formulated with different active ingredients.

DUREDAS is a bilayer tableting technology that may be used to formulate an active agent. DUREDAS was developed to provide for two different release rates, or dual release of a drug from one dosage form. The term bilayer refers to two separate direct compression events that take place during the tableting process. In an exemplary embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of an active agent may be desirable in order to facilitate a fast onset of therapeutic affect. Hence one layer of the tablet may be formulated as an immediate release granulate. By contrast, the second layer of the tablet may release the drug in a controlled manner, e.g., through the use of hydrophilic polymers. This controlled release may result from a combination of diffusion and erosion through the hydrophilic polymer matrix.

A further extension of DUREDAS technology is the production of controlled release combination dosage forms. In this instance, two different active agents may be incorporated into the bilayer tablet and the release of drug from each layer controlled to maximize therapeutic affect of the combination.

An active agent can be incorporated into any one of the aforementioned controlled released dosage forms, or other conventional dosage forms. The amount of active agent contained in each dose can be adjusted, to meet the needs of the individual patient, and the indication. One of skill in the art and reading this disclosure will readily recognize how to adjust the level of active agent and the release rates in a controlled release formulation, in order to optimize delivery of an active agent and its bioavailability.

Inhalational Formulations

An active agent (a prodrug that is converted in the individual to salicylic acid and that inhibits acetylation of a Tau polypeptide in a cell that normally produces Tau (e.g., a neuronal cell and/or a glial cell)) will in some embodiments be administered to a patient by means of a pharmaceutical delivery system for the inhalation route. An active agent may be formulated in a form suitable for administration by inhalation. The inhalational route of administration provides the advantage that the inhaled drug can bypass the blood-brain barrier. The pharmaceutical delivery system is one that is suitable for respiratory therapy by delivery of an active agent to mucosal linings of the bronchi. An active agent can be delivered by a system that depends on the power of a compressed gas to expel the active agent from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains an active agent, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

An active agent can also be formulated for delivery with a nebulizer, which is an instrument that generates very fine liquid particles of substantially uniform size in a gas. For example, a liquid containing an active agent is dispersed as droplets. The small droplets can be carried by a current of air through an outlet tube of the nebulizer. The resulting mist penetrates into the respiratory tract of the patient.

A powder composition containing an active agent, with or without a lubricant, carrier, or propellant, can be administered to a mammal in need of therapy. This embodiment can be carried out with a conventional device for administering a powder pharmaceutical composition by inhalation. For example, a powder mixture of the active agent and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with the present disclosure. An active agent can be formulated in basically three different types of formulations for inhalation. First, an active agent can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, an active agent can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166.

An active agent can be formulated into dry powder formulations. Such formulations can be administered by simply inhaling the dry powder formulation after creating an aerosol mist of the powder. Technology for carrying such out is described within U.S. Pat. Nos. 5,775,320 5,740,794.

Dosages

Although the dosage used will vary depending on the clinical goals to be achieved, a suitable dosage range of an active agent (a prodrug that is converted in the individual to salicylic acid and that inhibits acetylation of a Tau polypeptide in a cell that normally produces Tau (e.g., a neuronal cell and/or a glial cell)) is one which provides up to about 1 µg to about 1,000 µg or about 10,000 µg of the active agent and can be administered in a single dose. Alternatively, a target dosage of an active agent can be considered to be about in the range of about 0.1-1000 µM, about 0.5-500 µM, about 1-100 µM, or about 5-50 µM in a sample of host blood drawn within the first 24-48 hours after administration of the agent.

In some cases, a suitable dosage is in a range of from about 50 mg/kg to about 500 mg/kg, e.g., from about 50 mg/kg to 75 mg/kg, from 75 mg/kg to 100 mg/kg, from 100 mg/kg to 150 mg/kg, from 150 mg/kg to 200 mg/kg, from 200 mg/kg to 250 mg/kg, from 250 mg/kg to 300 mg/kg, from 300 mg/kg to 350 mg/kg, from 350 mg/kg to 400 mg/kg, from 400 mg/kg to 450 mg/kg, or from 450 mg/kg to 500 mg/kg.

In some cases, multiple doses of an active agent are administered. For example, in some cases, an active agent (a prodrug that is converted in the individual to salicylic acid and that inhibits acetylation of a Tau polypeptide in a cell that normally produces Tau (e.g., a neuronal cell and/or a glial cell)) is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some cases, the active agent is administered substantially continuously, using, e.g., an osmotic pump.

In some cases, an active agent (a prodrug that is converted in the individual to salicylic acid and that inhibits acetylation of a Tau polypeptide in a cell that normally produces Tau (e.g., a neuronal cell and/or a glial cell)) is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The active agent can be administered tid, bid, qd, qod, biw, tiw, qw, qow, three times per month, once monthly, substantially continuously, or continuously.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An active agent (a prodrug that is converted in the individual to salicylic acid and that inhibits acetylation of a Tau polypeptide in a cell that normally produces Tau (e.g., a neuronal cell and/or a glial cell)) is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, rectal, nasal, oral and other enteral and parenteral routes of administration. Routes of administration may be combined, if desired, or adjusted depending upon the agent and/or the desired effect. The active agent can be administered in a single dose or in multiple doses. In some embodiments, the active agent is administered orally. In other specific embodiments, the active agent is administered via an inhalational route. In some embodiments, the active agent is administered intranasally.

The active agent can be administered to a host using any available conventional methods and routes suitable for delivery of conventional drugs, including systemic or localized routes. In general, routes of administration contemplated by the present disclosure include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The active agent can also be delivered to the subject by enteral administration. Enteral routes of administration include, but are not necessarily limited to, oral and rectal (e.g., using a suppository) delivery.

Methods of administration of the active agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a tauopathy. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of subjects (wherein the term "subject" is used interchangeably herein with the terms "individual," "host," and "patient") are treatable according to the subject methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subject will be a human.

Subjects Suitable for Treatment

Individuals suitable for treatment with a subject treatment method include individuals who have been diagnosed with a tauopathy; individuals who have a tauopathy and who have been treated with an agent other than an agent discussed herein and who have either failed to respond to such treatment or who initially responded and subsequently relapsed.

Individuals suitable for treatment with a subject treatment method include individuals who have been diagnosed with Alzheimer's disease, Creutzfeldt-Jakob disease, dementia pugilistica, Down's syndrome, Gerstmann-Sträussler-Scheinker disease, inclusion body myositis, and prion protein cerebral amyloid angiopathy; a disease without distinct amyloid pathology, e.g., amyotrophic lateral sclerosis/Parkinsonism-dementia complex, argyrophilic grain dementia, corticobasal degeneration, diffuse neurofibrillary tangles with calcification, frontotemporal dementia with Parkinsonism linked to chromosome 17, Hallevorden-Spatz disease, multiple system atrophy, Niemann-Pick disease type C, Pick's disease, progressive subcortical gliosis, progressive supranuclear palsy, subacute sclerosing panencephalitis, or tangle-predominant Alzheimer's disease.

Non-Limiting Aspects of the Disclosure

Aspects, including embodiments, of the subject matter described herein may be beneficial alone or in combination, with one or more other aspects or embodiments. Without limiting the description, certain non-limiting aspects of the disclosure numbered 1-15 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A method for reducing the level of acetylated Tau in a neuron or a glial cell in an individual, the method comprising administering to the individual an effective amount of a prodrug that is converted in the individual to salicylate, wherein said administering provides for a reduction in the level of acetylated Tau in the neuron or the glial cell in the individual.
2. The method of 1, wherein said reduction treats a tauopathy in the individual.
3. The method of 2, wherein the tauopathy is frontotemporal dementia, Alzheimer's disease, progressive supranuclear palsy, corticobasal degeneration, Down syndrome, dementia pugilistica, inclusion-body myositis, or frontotemporal lobar degeneration.
4. The method of 1, wherein the prodrug is salsalate.
5. The method of 1, wherein the prodrug is a conjugate comprising salicylic acid covalently linked to D-glucose.
6. The method of 1, wherein the prodrug is a cyclic dimer of salicylic acid.
7. The method of 1, wherein the prodrug is a conjugate comprising salicylic acid covalently linked to an apolipoprotein.
8. The method of 1, wherein the prodrug is a conjugate comprising salicylic acid covalently linked to a large amino acid.
9. The method of 1, wherein the prodrug is a conjugate comprising salicylic acid covalently linked to a lysophosphatidylcholine.
10. The method of any one of 1-9, wherein the prodrug is conjugated to, or adsorbed onto, a nanoparticle.
11. The method of 10, wherein the nanoparticle is a poly(butyl cyanoacrylate) nanoparticle.
12. The method of 10 or 11, wherein the nanoparticle is a polysorbate 80-coated nanoparticle.
13. The method of any one of 1-9, wherein the prodrug is formulated with a lipid.
14. The method of 13, wherein the prodrug is encapsulated within a liposome.
15. The method of any one of 1-14, wherein the prodrug is administered via oral administration.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Materials and Methods

The following materials and methods were used in the examples described below.

Mice

For AAV-Tau (adeno-associated virus encoding Tau) injection experiments, only male mice were purchased from Jackson Laboratory with the same age and genetic background (C57BL/6) and used for all the experiments. The mice were housed in a pathogen-free barrier facility at UCSF with a 12-h light/dark cycle and ad libitum access to food and water. All behavior experiments were performed during daylight hours. All animal procedures were carried out under University of California, San Francisco, Institutional Animal Care and Use Committee-approved guidelines.

For SSA treatment experiments, only female PS19 mice obtained from Jackson Laboratory were used. The mice were housed in a conventional facility at Stanford University (Palo Alto, Calif.<USA) with a 12-h light/dark reverse cycle and ad libitum access to food and water. All behavior experiments of PS19 mice were performed during daylight hours and carried out under Stanford University School of Medicine, Institutional Animal Care and Use Committee-approved guidelines.

PK Analyses of Salsalate (SSA) and Salicylic Acid (SA) in Brain and Plasma

SSA was administered to C57B6 mice via oral gavage as a single bolus dose. Mice were sacrificed at predetermined time points and plasma and brain tissue samples were harvested for analysis by PPL labs (Redwood City, Calif., USA). SSA and its metabolite SA were measured simultaneously using oxopropanoyloxy benzoic acid as an internal standard solution. To extract SSA/SA from brain, 200 µl of 50% Acetonitrile in 0.1% formic acid was added to 30-50 mg of cortical tissue, followed by homogenization and vortexing. After addition of 200 µl of the internal standard solution, the samples were centrifuged and the supernatants were transferred for injection. To measure SSA/SA in the plasma, 10 µl of plasma samples were mixed with 90 µl $H_2O$ and 100 µl of Internal Standard Solution, followed by centrifugation and injection. HPLC was performed using a C18 column following a gradient program (10% to 90% acetonitrile over a period of 6 min) with a flow rate of 0.4 ml/min. The injection volume was ~5 µl. Mass spectrometry analyses were performed on 3200 Q TRAP system (AB SCIEX, Framingham, Mass. USA.) using an MQL algorithm.

Behavioral Tests

Morris Water Maze.

Experimenters were blind to the genotypes or treatments of the mice for all behavioral analyses. The water maze consisted of a pool (122 cm in diameter) containing opaque water (20±1° C.) and a platform (14 cm in diameter) submerged 1.5 cm under the water. Hidden platform training (days 1-5) consisted of 10 sessions (two per day, 2 h apart), each with three trials. The mouse was placed into the pool at alternating drop locations for each trial. A trial ended when the mouse located the platform. The maximum trial time was 60 s per trial. Mice that failed to find the platform within a 60 s trial were led to it and placed on it for 15 s.

After the initial learning task, a reversal learning protocol (days R1-R4; two per day, 2 h apart) was conducted for the same mice. The hidden platform was moved to the opposite quadrant for reversal learning. For the probe trial, 48 h after the final reversal training trial, mice were returned to the pool with a new drop location in the absence of the hidden platform. Performance was measured with an EthoVision video-tracking system (Noldus Information Technology). Visible platform training, where the platform was cued with a mounted black-and-white striped mast, was conducted for four trials after completion of probe trials. Mice that floated, and did not swim, were excluded from analysis.

Small Y-Maze.

Mice were placed in the center of a small Y-maze (arm length: 15 cm) and spontaneous alternation was recorded in a single continuous 6 min trial by a live observer. Each of the three arms was designated a letter A-C, and entries into the arms were recorded. The percent of spontaneous alternation was calculated over the total number of entries possible. The apparatus was cleaned with 70% ethanol between trials.

Open Field Test.

Mice were placed individually into brightly lit automated activity cages equipped with rows of infrared photocells interfaced with a computer (San Diego Instruments). After a 1-min adaptation period, open field activity was recorded for 20 min. Recorded beam breaks were used to calculate active times, path lengths, rearing times, and rearing events. After behavioral testing, the apparatus was cleaned with 70% ethanol between trials.

Fixed Location Dry Maze.

The Fixed Location Dry Maze is also called DMP dry maze (Faizi, M., et al. *Brain Behav* 2, 142-154 (2012)). Experiments were performed at an animal facility at Stanford University (Palo Alto, Calif.). Mice were housed at a standard temperature (22±1° C.), in a reverse light-controlled environment (lights off from 8:30 am to 8:30 pm) with ad libitum access to food and water. Animals are group-housed with minimal enrichment such as shelter (paper towel tubes and nestlets). The experimenter remained blinded to the experimental groups throughout the entire study. A custom built dry maze was used, which is a 122 cm diameter circular platform with 40 escape holes (5 cm in diameter). The target escape tube was attached to one of these holes; all other holes except the target escape hole are left open. High overhead lighting (~750 lux) and air turbulence created by fans were used as aversive stimuli to encourage the animals to seek out the target escape hole. All aversive stimuli were turned off when the mouse entered the target escape hole. Visual cues were provided around the maze for navigation. The subjects were monitored by a video tracking system directly above maze, and the parameters were measured using the computer software Ethovision. Subjects were given four trials to find the target escape hole with a 2-min inter-trial-interval. Each trial was 90 s long. Animals that could not find the escape hole were led by the experimenter and allowed to enter the target escape hole. After each trial, the apparatus was cleaned with 1% Virkon to eliminate odor cues. After 2 days of training and 3 days of learning, mice were tested in a probe trial. During the probe, the escape tube was removed from the maze and the mice were allowed to explore. Time in each quadrant was recorded and memory was assessed by the time spent in the target quadrant versus the other three quadrants.

Statistical Analysis

Data were analyzed with GraphPad Prism v.5 (GraphPad) or Stata. Differences between means were assessed with paired or unpaired Student's t test, one-way or two-way analysis of variance, followed by post hoc testing of all pairwise comparisons among genotypes (with Tukey-Kramer correction for one-way ANOVA and Bonferroni correction for two-way ANOVA), or by mixed effects model, as indicated. Pearson's correlation coefficients were used to quantify the linear relationship between two variables. The Shapiro-Wilk test of normality was applied to all data sets, and in cases where the data did not demonstrate a normal distribution, non-parametric tests were used to analyze statistical differences. The Mann-Whitney test was used for unpaired t-tests, the Wilcoxon matched pairs test was used for paired comparisons, and the Kruskal-Wallis test was used for ANOVAs. Multilevel mixed-effects linear regression model fit using STATA12 were used to compare habituation curves in the open field test and learning curves in MWM and fixed location dry maze; random intercepts and linear time slopes for each mouse were taken into account for the correlation among repeated observations. All samples or animals were included for statistical analysis unless otherwise noted.

Results

Example 1

Salicylate Treatment Inhibits p300 and Reduces Acetylated TauK174 In Vitro

Salicylic acid (salicylate) has recently been identified as a p300 inhibitor. To examine the effects of salicylate treatment on tau acetylation and phosphorylation, HEK293 cells overexpressing hTau (WT) and p300 were treated with sodium salicylate (SS). Ac-tau was significantly reduced by salicylate in a dose-dependent manner (FIG. 1a, 1b). Salicylate treatment also reduced AT8-positive phospho-tau (FIG. 1a, 1b). Similar effects were observed in primary neurons infected with lenti-hTau (WT) (FIG. 1c, 1d). These results demonstrate that salicylate can reduce tau acetylation and phosphorylation in vitro.

FIGS. 1A-1D. Salicylate inhibits p300 and reduces ac-tau and p-tau in vitro (FIG. 1A) HEK293 cells overexpressing wild-type human tau were treated with 0, 5, 10 mM salicylate for 24 hr. Representative Western blot of four experiments. (FIG. 1B) Quantification of ac-tau and p-tau levels in HEK293 cells treated with salicylate. ac-tau/t-tau, p-tau/t-tau in non-treated cells were set as 1. n=4. , $p<0.01$, *, $p<0.001$ (two-tails unpaired t-test). Error bar, S.E.M. (FIG. 1C) Rat primary cortical neurons infected with lenti-hTau (WT) were treated with 0, 5, or 10 mM salicylate for 24 hr. Representative Western blot of four experiments. (FIG. 1D) Quantification of ac-tau, p-tau and p300 levels in primary neurons treated with salicylate. ac-tau/t-tau, p-tau/t-tau and p300/GAPDH in non-treated cells were set as 1. n=4. *, $p<0.05$, , $p<0.01$, *, $p<0.001$ (two-tails unpaired t-test). Error bar, S.E.M.

Example 2

The K174Q Mutation Abolishes the Tau-Lowering Effects of Salicylate in Primary Neurons.

As shown in FIGS. 2A and 2B, mutating amino acid K174 to glutamine (Q) abolished the tau-lowering effects of salicylate in primary neurons.

Example 3

Salsalate Treatment in PS19 Mice Improves Hippocampus-Dependent Cognitive Behavior.

Salsalate (SSA) is an FDA-approved non-steroidal anti-inflammatory drug, which serves as a pro-drug for salicylate. Pharmacokinetic analysis showed that upon absorption, salsalate readily penetrates into the brain and gives rise to a relatively stable level of salicylate over 8 hours. It was investigated whether salsalate treatment lowers levels of ac-tau in vivo. 7-8 month old PS19 mice were dosed with salsalate (225 mg/kg) or vehicle by oral gavage for 8 weeks (FIG. 3A). The 225 mg/kg dosage was previously reported as 300 mg/kg, which calculation did not account for the presence of fillers. 225 mg/kg represents the administered dose of salsalate. Of note, the human equivalent dose of 225 mg/kg in this example is ~1350 mg/day for a 75 kg person, lower than the dose typically prescribed to human patients (3000 mg/day).

Figure 3B:
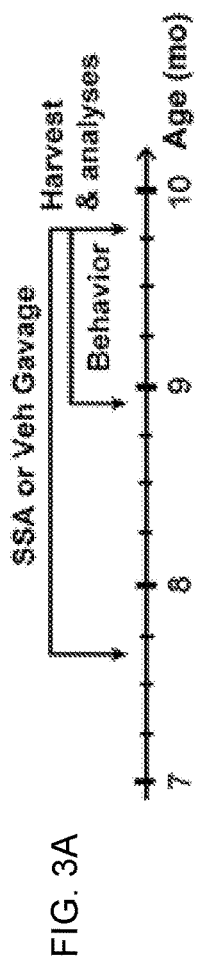
Figure 3C:
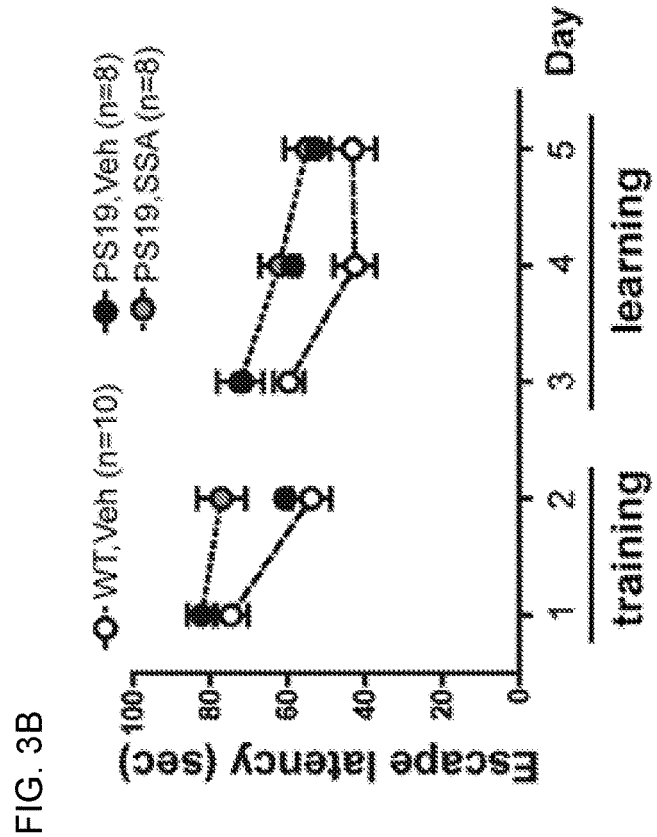

The effects of salsalate treatment on tau-mediated behavioral deficits were assessed. In Fixed Location Dry Maze, PS19 mice treated with vehicle showed impaired spatial learning compared with their wild-type littermates treated with vehicle (FIG. 3B), consistent with previous findings in the Morris Water Maze. Salsalate treatment did not rescue the learning deficit of PS19 mice (FIG. 3B). Subsequent statistical analysis indicated that the impaired spatial learning seen in the Fixed Location Dry Maze test did not reach statistical significance. In the probe trial, wild-type mice treated with vehicle spent significantly more time within the target quadrant than the non-target quadrant (FIG. 3C). In contrast, PS19 mice treated with vehicle spent equal amount of time within the target and non-target quadrants, exhibiting significant impairment in memory retention (FIG. 3C). Remarkably, PS19 mice treated with salsalate significantly rescued the deficit (FIG. 3C). Similar results (not shown) were obtained using the Morris Water Maze protocol.

FIGS. 3A-3C. Salsalate Treatment in PS19 Mice Improves Spatial Memory.

(FIG. 3A) Experimental plan for gavage treatment of salsalate or vehicle. (FIG. 3B) Learning curve of PS19 mice and WT mice treated with salsalate or vehicle. Day 1-2, training; Day 3-5, learning. (FIG. 3C) Effect of salsalate treatment on spatial memory deficit in PS19 mice. (***, $p<0.001$). (*, $p<0.05$). WT, veh: n=10. PS19, Veh: n=8. PS19, SSA: n=8. This example supports the clinical evaluation of SSA and its derivatives as therapies in human tauopathies.

Example 4

Salsalate Treatment in PS19 Mice Prevents or Rescues Neuronal Loss in Hippocampus.

The neurodegeneration phenotype of PS19 mice was examined by measuring hippocampal volume and NeuN-positive cell number. Compared with wild-type littermates, 10 months old PS19 mice treated with vehicle had significant loss of hippocampal volume (FIG. 4A), exhibiting a severe neurodegenerative phenotype. In contrast, PS19 mice treated with salsalate did not show any hippocampal volume loss (FIG. 4A). Similarly, the number of NeuN-positive cells in the hippocampal section of PS19 mice treated with vehicle was significantly lower compared with their wild-type littermates, whereas salsalate-treated PS19 did not show any significant difference compared to wild-type (FIG. 4B). The number of NeuN-positive cells in the hippocampus positively correlates with time spent in the target quadrant in the dry maze (FIG. 4C), suggesting a strong correlation of the hippocampal neuron number and the spatial memory.

FIGS. 4A-4C. Salsalate Treatment in PS19 Mice Prevents or Rescues Neuronal Loss in Hippocampus.

(FIG. 4A) 10 months old PS19 mice have significant hippocampal volume loss compared to wild-type, which is absent in SSA-treated group. Left. Representative nissl staining of hippocampus from vehicle-treated WT, vehicle-treated PS19 and SSA-treated PS19 mice. ***, $p<0.001$, *, $p<0.05$ (two-tails unpaired t-test). Error bar, S.E.M. Scale bar, 500 um. (FIG. 4B) 10 months old PS19 mice have significant reduction of NeuN-positive cells compared to wild-type, which is absent in SSA-treated group. Left. Representative NeuN staining of hippocampus from vehicle-treated WT, vehicle-treated PS19 and SSA-treated PS19 mice. **, $p<0.01$ (two-tails unpaired t-test). Error bar, S.E.M. (FIG. 4C) NeuN number positively correlates with time spent in target quadrant in dry maze. $p=0.0142$ (linear regression).

Example 5

Salsalate Treatment in PS19 Mice Inhibits p300 Activity and Reduces Tau Acetylation.

Figure 5A:
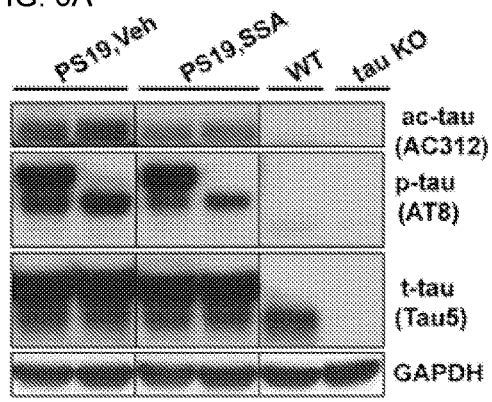
FIGS. 5A-5D depict the effect of salsalate on p300 activity and tau acetylation in vivo.
Figure 5B:
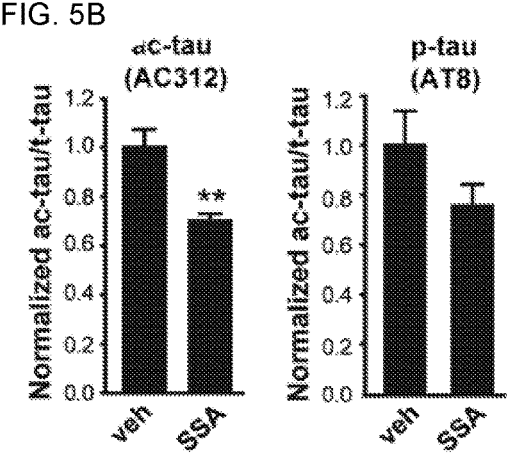
Figure 5C:
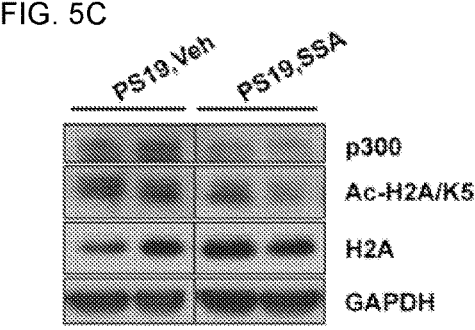
Figure 5D:
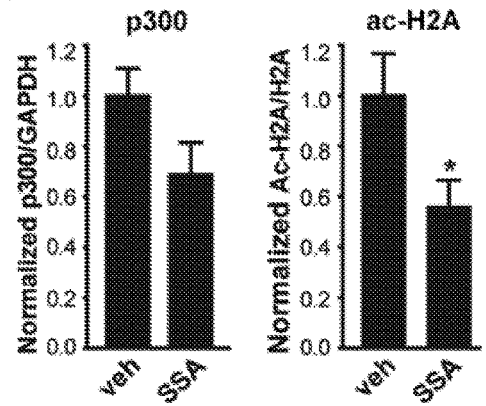

The levels of ac-tau and phospho-tau in the hippocampal lysate of PS19 mice were examined (FIG. 5A). Compared to vehicle-treated group, salsalate-treated group had significantly lower ac-tau levels (FIGS. 5A and 5B). There was a trend of reduction in AT-8 positive phospho-tau levels, although the difference was not significant (FIGS. 5A and 5B). Salsalate treatment lead to a trend of reduction in p300 levels, as well as a significant reduction of p300 HAT activity as measured by levels of histone acetylation (FIGS. 5C and 5D), consistent with the finding that salicylate inhibits p300 activity (Shirakawa et al., unpublished). Taken together, these data demonstrate that salsalate treatment effectively lowered levels of ac-tau and improved cognitive deficits, after disease onset in PS19 mice.

FIGS. 5A-5D.

Salsalate treatment in PS19 mice inhibits p300 activity and reduces tau acetylation. (FIG. 5A) Representative Western blot showing levels of ac-tau, p-tau, t-tau and GAPDH in brain lysate of PS19 mice treated with salsalate (SSA) or vehicle (veh). Wild-type (WT) littermates treated with vehicle and tau knockout (KO) mice were included as controls. (FIG. 5B) Quantification of ac-tau and p-tau levels in brain lysate of PS19 mice treated with vehicle or salsalate. ac-tau/t-tau and p-tau/t-tau in vehicle-treated group were set as 1. n=8. **, $p<0.01$ (two-tails unpaired t-test). Error bar, S.E.M. (FIG. 5C) Representative Western blot showing levels of p300, ac-H2A(K5), H2A and GAPDH in brain lysate of PS19 mice treated with salsalate (SSA) or vehicle (veh). (FIG. 5D) Quantification of p300 and ac-H2A levels in brain lysate of PS19 mice treated with vehicle or salsalate. p300/GAPDH and ac-H2A/H2A in vehicle-treated group were set as 1. n=8. *, $p<0.05$ (two-tails unpaired t-test). Error bar, S.E.M.

Example 6

Figure 8:
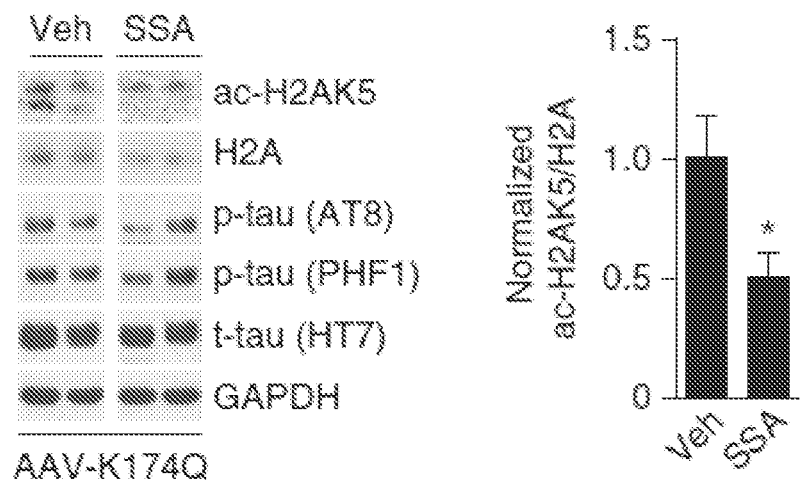
FIG. 8 provides (Left) an immunoblot analysis of ac-H2AK5, H2A, p-tau (AT8 and PHF-1), t-tau (HT7) and GAPDH in mice infected with AAV-K174Q and treated with SSA or vehicle; and (Right) a graph depicting the results of a quantification of ac-H2AK5 and H2A. n=11 (vehicle) or 10 (SSA) mice; *P<0.05, unpaired Student's t-test; values are mean±s.e.m.
Figure 9:
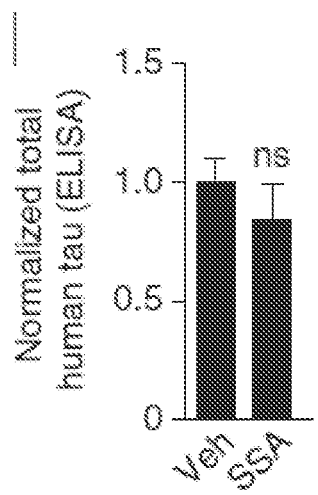
FIG. 9 provides a graph showing results indicating that SSA treatment failed to reduce levels of t-tau in K174Q injected mice compared to vehicle treated controls. ELISA analysis of K174Q tau after SSA treatment. n=11 (vehicle) or 10 (SSA) mice; ns, not significant; P=0.3647; unpaired Student's t-test; values are mean±s.e.m.
Figure 10:
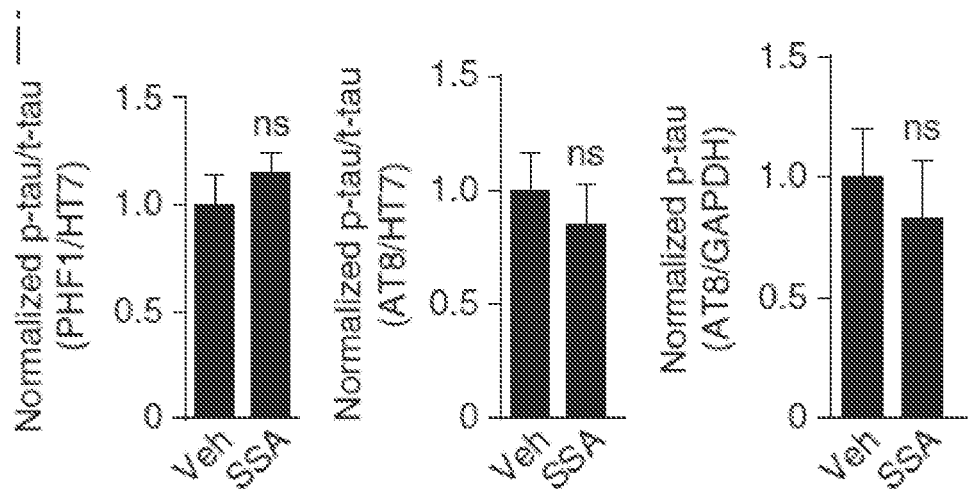
FIG. 10 provides graphs showing that levels of PHF1-positive p-tau relative to t-tau, or AT8-positive p-tau normalized by t-tau or GAPDH, were not affected by SSA treatment. Levels of PHF-1-positive p-tau normalized to HT7 (left) or AT8-positive p-tau normalized to HT7 (middle) or GAPDH (right) after SSA treatment. n=11 (vehicle) or 10 (SSA) mice; ns, not significant, unpaired Student's t-test. Values are mean±s.e.m.
Figure 11:
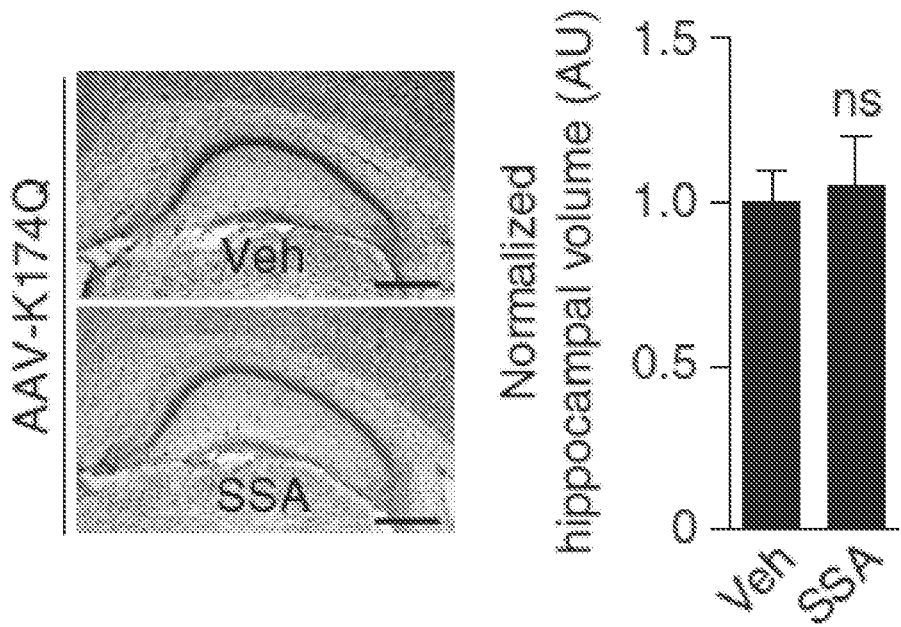
FIG. 11 provides hippocampal staining images and a graph showing that SSA failed to prevent/reduce hippocampal atrophy in AAV-K174Q-injected mice. Nissl staining (left) and hippocampal volume (right) in mice expressing K174Q tau after SSA treatment. Scale bars, 500 µm; n=11 (vehicle) or 10 (SSA) mice; ns, not significant, unpaired Student's t-test. Values are mean±s.e.m.

Ac-K174 Inhibition as a Mediator of Salicylate/SSA's Tau-Lowering and Protective Effects To determine if SSA's beneficial effects involve inhibition of ac-K174 in vivo. Two-month after injecting with AAV-K174Q, mice were treated with SSA daily as previously performed in PS19 mice. Ac-H2AK5 levels were reduced in the SSA-treated group, confirming inhibition of p300 by SSA (FIG. 8). In contrast to the tau-lowering effects of SSA in PS19 mice, SSA treatment failed to reduce levels of t-tau in K174Q injected mice compared to vehicle treated controls (FIG. 9). Levels of PHF1-positive p-tau relative to t-tau, or AT8-positive p-tau normalized by t-tau or GAPDH, were also not affected by SSA treatment (FIG. 10). Moreover, SSA failed to prevent/reduce hippocampal atrophy in AAV-K174Q-injected mice (FIG. 11), supporting the importance of ac-K174 inhibition in SSA's protective effects.

Example 7

SSA Protects Against Pathological Alterations in PS19 Mice

Experiments were conducted to determine whether inhibiting K174 tau acetylation ameliorates tau-mediated pathological deficits in vivo.

Prominent NFTs and dystrophic neurites, positive for Gallyas silver staining, were detected throughout the forebrains in PS19 mice (FIG. 12A). SSA reduced the number of Gallyas silver-positive neurons and neurites in the cortex and hippocampus of PS19 mice, in both female (FIGS. 12A and 12B), and male cohorts (data not shown).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for reducing the level of acetylated Tau in a neuron or a glial cell in an individual, the method comprising administering to the individual an effective amount of a prodrug that is converted in the individual to salicylate, wherein said administering provides for a reduction in the level of acetylated Tau in the neuron or the glial cell in the individual.

2. The method of claim 1, wherein said reduction treats a tauopathy in the individual.

3. The method of claim 2, wherein the tauopathy is frontotemporal dementia, Alzheimer's disease, progressive supranuclear palsy, corticobasal degeneration, Down syndrome, dementia pugilistica, inclusion-body myositis, or frontotemporal lobar degeneration.

4. The method of claim 1, wherein the prodrug is salsalate.

5. The method of claim 1, wherein the prodrug is a conjugate comprising salicylic acid covalently linked to D-glucose.

6. The method of claim 1, wherein the prodrug is a cyclic dimer of salicylic acid.

7. The method of claim 1, wherein the prodrug is a conjugate comprising salicylic acid covalently linked to an apolipoprotein.

8. The method of claim 1, wherein the prodrug is a conjugate comprising salicylic acid covalently linked to a large amino acid.

9. The method of claim 1, wherein the prodrug is a conjugate comprising salicylic acid covalently linked to a lysophosphatidylcholine.

10. The method of claim 1, wherein the prodrug is conjugated to, or adsorbed onto, a nanoparticle.

11. The method of claim 10, wherein the nanoparticle is a poly(butyl cyanoacrylate) nanoparticle.

12. The method of claim 10, wherein the nanoparticle is a polysorbate 80-coated nanoparticle.

13. The method of claim 1, wherein the prodrug is formulated with a lipid.

14. The method of claim 13, wherein the prodrug is encapsulated within a liposome.

15. The method of claim 1, wherein the prodrug is administered via oral administration.

16. The method of claim 4, wherein the prodrug is conjugated to, or adsorbed onto, a nanoparticle.

17. The method of claim 16, wherein the nanoparticle is a poly(butyl cyanoacrylate) nanoparticle.

18. The method of claim 17, wherein the nanoparticle is a polysorbate 80-coated nanoparticle.

19. The method of claim 4, wherein the prodrug is formulated with a lipid.

20. The method of claim 19, wherein the prodrug is encapsulated within a liposome.

* * * * *